US006803500B1

(12) United States Patent
Iida et al.

(10) Patent No.: US 6,803,500 B1
(45) Date of Patent: Oct. 12, 2004

(54) GENES ENCODING PROTEINS REGULATING THE PH OF VACUOLES

(75) Inventors: Shigeru Iida, Okazaki (JP); Sachiko Tanaka, Okazaki (JP); Yoshishige Inagaki, Okazaki (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/830,123

(22) PCT Filed: Aug. 24, 1999

(86) PCT No.: PCT/JP00/05722

§ 371 (c)(1),
(2), (4) Date: Apr. 24, 2001

(87) PCT Pub. No.: WO01/14560

PCT Pub. Date: Mar. 1, 2001

(30) Foreign Application Priority Data

Aug. 24, 1999 (JP) .......................................... 11-236800

(51) Int. Cl.[7] ........................ C12N 15/29; C12N 15/82; A01H 5/00; A01H 5/02

(52) U.S. Cl. ....................... 800/282; 800/298; 800/323; 536/23.6; 435/320.1; 435/419; 435/468; 435/252.3

(58) Field of Search ...................... 424/93.2; 435/320.1, 435/419, 468, 252.3; 536/23.6; 800/282, 298, 323

(56) References Cited

U.S. PATENT DOCUMENTS 5,910,627 A * 6/1999 Chuck et al. ............... 800/205

FOREIGN PATENT DOCUMENTS

WO 94/23561 10/1994

OTHER PUBLICATIONS

Rhoads et al. Regulation of the cyanide–resistant alternative oxidase of plant mitochondria. J. Biol. Chem., Nov. 1998, vol. 273, No. 46, pp. 30750–30756.*

A. Fukuda et al, "Molecular cloning and expression of the Na +/H + exchanger gene in *Oryza sativa*" Biochim. Biophys. Acta, vol. 1446, pp. 149–155, Jul. 1999.

R. Gaxiola et al, "The *Arabidopsis thaliana* proton transporters, AtNhxL and Avpl, can function in cation detoxification in yeast", Proc. Natl. Acad. Sci. USA, vol. 96, pp. 1480–1485, Feb. 1999.

Y. Lu et al, "AtMRPI gene of Arabidopsis encodes a glutathione S–conjugate pump: Isolation and functional definition of a plant ATP–binding cassette transporter gene", Proc. Natl. Acad. Sci. USA, vol. 94, pp. 8243–8248, Jul. 1997.

K. Marrs et al, "A glutathione S–transferase involved in vacuolar transfer encoded by the maize gene Bronze–2", Nature, vol. 375, No. 6530, pp. 397–400, Jun. 1995.

S. Tanaka et al, "Colour–enhancing protein in blue petals", Nature, vol. 407, p. 581, Oct. 2000.

* cited by examiner

*Primary Examiner*—David T. Fox
*Assistant Examiner*—Cynthia Collins
(74) *Attorney, Agent, or Firm*—Burns, Doane, Swecker & Mathis, L.L.P.

(57) ABSTRACT

There is provided a gene encoding a protein that has an activity of regulating the pH of vacuoles, for example a gene derived from morning glory encoding a protein that has the amino acid sequence as set forth in SEQ ID NO: 2. By introducing this gene into a plant, the flower color can be regulated via the control of the pH of vacuoles.

7 Claims, 3 Drawing Sheets

GENES ENCODING PROTEINS REGULATING THE PH OF VACUOLES

TECHNICAL FIELD

The present invention relates to genes encoding proteins that regulate the pH of vacuoles, and the uses thereof.

BACKGROUND

In the flower industry, the development of novel or varied cultivars of flowering plants is important, and flower color is one of the most important traits of flowers. Although cultivars of various colors have been bred using conventional breeding by crossing, it is rare that a single plant species has cultivars of all colors. Thus, there is a need for the development of cultivars having a variety of colors.

The main components of flower color are a group of flavonoid compounds termed anthocyanins. It is known that a variety of anthocyanins occur in plants, and the structure of many of them have already been determined. The color of anthocyanins depends partly on their structures. Progress has been made in the study on the enzymes and genes involved in the biosynthesis of anthocyahins, and in some studies molecular biological techniques and gene introductions into plants were used to change the structure of anthocyanins, leading to changes in the color of flowers (Holton and Cornish, Plant Cell, 7:1071 (1995); Tanaka et al., Plant Cell Physiol. 39:1119 (1998)). The color of anthocyanins also depends on the pH of the aqueous solution, and the same anthocyanin may appear blue when the pH of the aqueous solution is neutral to weakly alkaline (Saito and Honda, Genda Kadaku (Chemistry Today), May 1998, pp. 25).

It is also known that since anthocyanins are present in the vacuole of the cell, the pH of vacuoles has a great impact on the color of flowers (Holton and Cornish, Plant Cell, 7 (1995); Mol et al., Trends Plant Sci. 3:212 (1998)). For example, in morning glory (Ipomea tricolor), it is known that the reason why red-purple buds bloom into blue flowers is that the pH of vacuoles in petal epithelium rises from 6.6 to 7.7 (Yoshida et al., Nature 373:291 (1995)).

It is thought that the vacuole of plant cells is regulated by vacuolar proton-transporting ATPase and vacuolar proton-transporting pyrophosphatase (Leigh et al., The Plant vacuole (1997), Academic Press), but the mechanism of how these proton pumps are involved in the color of flowers has not been elucidated. It was also known that a sodium ion-proton antiporter (hereinafter referred to as $Na^+$—$H^+$ antiporter) exits in plant vacuoles and that the $Na^+$—$H^+$ antiporter transports sodium ions into vacuoles, depending on the proton concentration gradient between the outside and the inside of vacuoles, whereupon protons are transported outside of vacuoles resulting a reduced proton concentration gradient.

Furthermore, the $Na^+$—$H^+$ antiporter is thought to be a protein with a molecular weight of about 170,000. However, there are many unknown factors involved in the regulation of pH of vacuoles, and the mechanism of regulating the pH of vacuoles, in particular the petal vacuoles, is uncertain (Leigh et al., The Plant Vacuole (1997), Academic Press). The pH of plant vacuoles has never been artificially raised, nor have any industrially useful traits been obtained, and its association with flower color is unknown.

It is known that the $Na^+$—$H^+$ antiporter gene, with a molecular weight of about 70,000, has been cloned from Arabidopsis, and a yeast into which this gene was introduced has acquired salt tolerance (Gaxiola et al., Proc. Natl. Acad. Sci. USA 96:1480–1485 (1999)), but it is not known how this antiporter regulates the pH of vacuoles in plant cells or how it is associated with flower color.

On the other hand, in petunias, seven loci are known to be involved in the pH regulation of petal vacuoles, and it has been proposed that the pH of petal vacuoles increases when one of them turns homozygously recessive (van Houwelingen et al., Plant J. 13:39 (1998); Mol et al., Trends Plant Sci. 3:212 (1998)). One of them, Ph6, has already been cloned and was found to be a kind of transcription regulating factor (Chuck et al., Plant Cell 5:371 (1993)), but the actual biochemical mechanism involved in the pH regulation of vacuoles is unknown.

In morning glory (Ipomea nil), the analysis of mutants revealed that a number of loci are associated with the color and shape of leaves and flowers and that 19 of them are highly mutable (Iida et al., Shokubutsu Saibo Kogaku Series (Plant Cell Engineering Series) 5 (1996) pp. 132, Shujunsha; Iida et al., Annal. New York Acad. Sci. (1999) pp. 870). Among them, the one locus defined by the recessive mutation that results in purple flowers instead of blue flowers is termed the Purple locus (T. Hagiwara, The genetics of flower colours in Phrarbitis nil. J. Coll. Agr. Imp. Univ. Tokyo 51:241–262 (1931); Y. Imai, Analysis of flower colour in Pharbitis nil. J. Genet. 24:203–224 (1931)), and one allele of mutable mutation that results in flowers that produce blue sectors in purple petals was termed purple-mutable (pr-m) (Imai, J. Coll. Agric. Imp. Univ. Tokyo 12:479 (1934)). The gene derived from the Purple locus is termed Purple gene.

The blue portion is believed to be derived from somatic reverse mutation from the recessive purple, and germ cell revertants can also be separated. An allele produced from the reverse mutation of these revertants are termed herein Purple-revertant (Pr-r). Such a classical method of genetic analysis had been performed on this Purple gene, but the identity of the Purple gene and its association etc. with the pH regulation of petal vacuoles were totally unknown.

It is believed that if the pH of vacuoles could be modified, for example if the pH of vacuoles could be raised, flower color could be turned blue. Representative plant species that lack blue colors include roses, chrysanthemums, carnations, gerberas and the like, which are very important cut flowers. Though the importance of modifying pH of vacuoles has been recognized, the identities of proteins that regulate the pH of petal vacuoles are unknown and therefore the isolation of genes encoding them has been in great demand.

DISCLOSURE OF THE INVENTION

The present invention provides a gene of a protein that regulates the pH of vacuoles in plant cells, preferably a gene of a protein that transports protons in vacuoles, more preferably a $Na^+$—$H^+$ antiporter gene. By introducing the gene of the present invention into a plant and allowing it to be expressed, flower color can be controlled and, preferably, can be turned blue.

Thus, the present invention provides a gene encoding a protein that regulates the pH of vacuoles. This gene is, preferably, a gene encoding a $Na^+$—$H^+$ antiporter, for example a gene encoding a protein that has the amino acid sequence as set forth in SEQ ID NO: 2, or a gene encoding a protein that has an amino acid sequence modified by the addition or deletion of one or a plurality of amino acids and/or substitution with other amino acids in the amino acid sequence as set forth in SEQ ID NO: 2 and that, has an activity of regulating the pH of vacuoles; a gene encoding a protein that has an amino acid sequence having a identity of 20% or more with the amino acid sequence as set forth in SEQ ID NO: 2 and that has an activity of regulating the pH of vacuoles; or, a gene that hybridizes to part or all of a nucleic acid having a nucleotide sequence encoding the amino acid sequence as set forth in SEQ ID NO: 2 under a stringent condition, and that encodes a protein having an activity of regulating the pH of vacuoles.

The present invention also provides a vector comprising the above gene.

The present invention also provides a host cell transformed with the above vector.

The present invention also provides a protein encoded by the above gene.

The present invention further provides a method of producing a protein that has an activity of regulating the pH of vacuoles, said method comprising culturing or growing the above host cell and then harvesting said protein from said host cell.

The present invention also provides a plant in which said gene or said vector has been introduced or a progeny thereof having the same property as said plant, or a tissue thereof.

The present invention also provides a cut flower of the above plant or a progeny thereof.

The present invention further provides a method of regulating the pH of vacuoles comprising introducing the above gene or the above vector into a plant or plant cells and then allowing it to be expressed.

The present invention further provides a method of controlling the flower color of plants comprising introducing the above gene or the above vector into a plant or plant cells and then allowing said gene to be expressed.

BEST MODE FOR CARRYING OUT THE INVENTION

Figure 1:
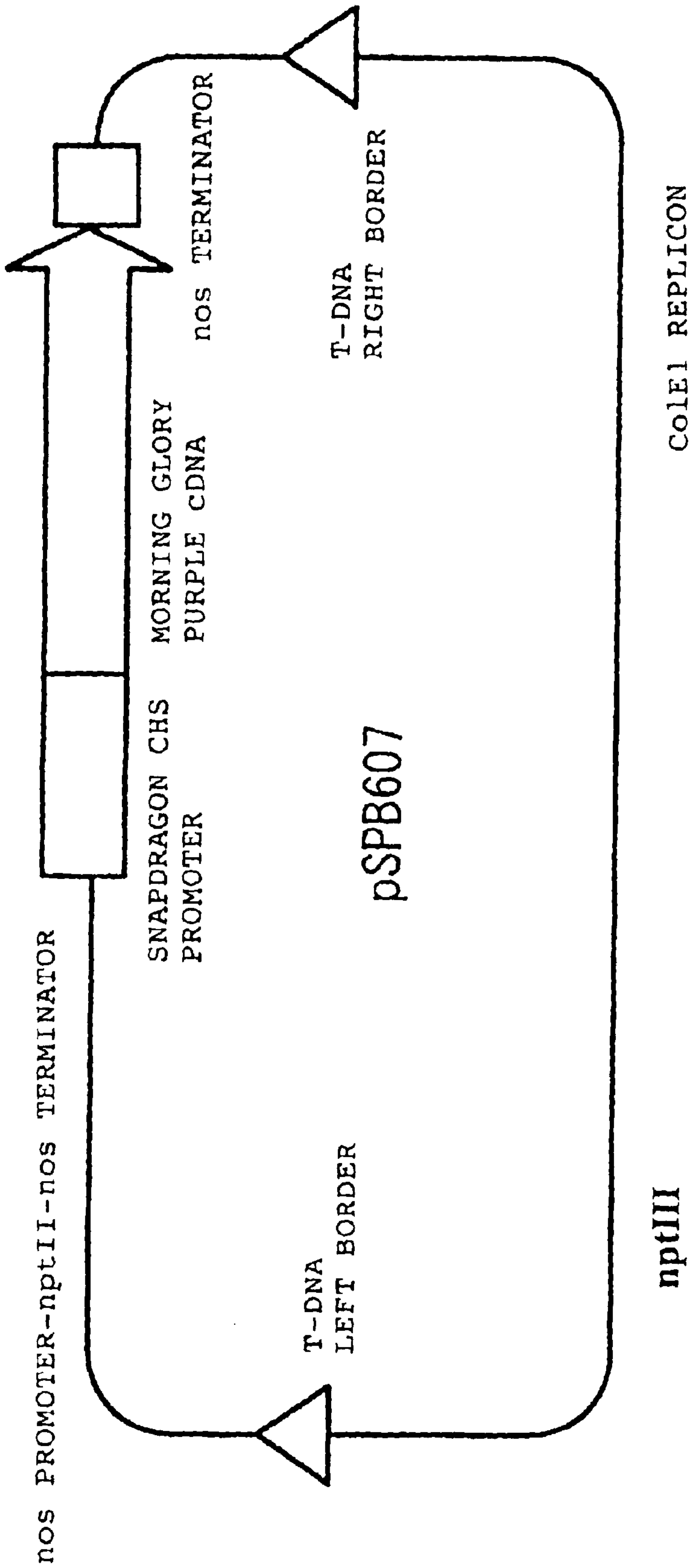
FIG. 1 is a drawing showing the structure of plasmid pSPB607.

The color of the petal of morning glory is blue when the locus Purple is dominant, and the blue petal turns purple when it is homozygously recessive. It is clear that the locus is associated with flower color but the mechanism thereof is unknown.

First, the chemical analysis of the pigments in the petal of the pr-m mutant and a revertant thereof detected no difference in the composition of the pigments. The change in flower color of the blue-colored morning glory from the reddish purple buds to the blue flowers accompanied by flowering is believced, as mentioned above, to be caused by pH changes in the vacuole of petal cells.

In the pr-m mutant, flowering is not associated with a color change to blue, and the pH of vacuoles of petal cells of flowers that bloomed was lower in the pr-m mutant than in Pr-r. Thus, the Purple gene is considered to be a gene that regulates the pH of vacuoles of petal cells dduring flowering thereby controls flower color. Accordingly, using a pr-m mutant, and a revertant thereof, by the transposon display method, fragments of genomic DNA containing the Purple gene sequence specifically present in pr-m were identified and then the Purple gene was identified. Surprisingly, the Purple gene thus obtained had a homology with the $Na^+$—$H^+$ antiporter from Arabidopsis etc., and, in the pr-m mutation, a transposon had been inserted in the 5'-untranslated region the Purple gene.

As the gene of the present invention, there can be mentioned, for example, one that encodes the amino acid sequence as set forth in SEQ ID NO: 2. It is known, however, that proteins having an amino acid sequence modified by the addition or deletion of one or a plurality of amino acids and/or substitution with other amino acids also retain an activity equal to that of the original protein. Thus in accordance with the present invention, a protein that has an amino acid sequence modified by the addition or deletion of one or a plurality of amino acids and/or substitution with other amino acids in the amino acid sequence as set forth in SEQ ID NO: 2, and a gene encoding said protein, are encompassed in the present invention as long as the protein is a protein that has an activity of regulating the pH of vacuoles.

The present invention also relates to a gene that hybridizes to the nucleotide sequence as set forth in SEQ ID NO: 1, a nucleotide sequence encoding the amino acid sequence as set forth in SEQ ID NO: 2, or a nucleotide sequence encoding part of these nucleotide sequences at a stringent condition, for example at 5×SSC and 50° C., and that encodes a protein having an activity of regulating the pH of vacuoles. As used herein, a suitable hybridization temperature varies with the nucleotide sequence and the length of the nucleotide sequence, and when, for example, a DNA fragment comprising 18 bases encoding 6 amino acids is used as a probe, a temperature of 50° C. or lower is preferred.

Genes selected, based on such hybridization, include those obtained from nature, for example from plants such as petunia and torenia, but a gene derived from sources other than plants may be used. Genes selected based on hybridization may be cDNA or genomic DNA.

The $Na^+$—$H^+$ antiporter genes form a superfamily (Debrov et al., FEBS Lett. 424:1 (1998)), and have an amino acid homology of 20% or more (Orlowski et al., J. Biol. Chem. 272:22373 (1997)).

Thus, the present invention relates to a gene encoding a protein that has an amino acid sequence with a homology of about 20% or more, preferably 50% or more, for example 60% or 70% or more, and that has an activity of regulating the pH of vacuoles.

A gene having an intact nucleotide sequence is obtained, as specifically illustrated in Examples, by, for example, screening CDNA libraries. DNA encoding a protein having a modified amino acid sequence can be synthesized by commonly used site-directed mutagenesis or the PCR method based on DNA having an intact nucleotide sequence. For example, a DNA fragment that is to be modified may-be obtained by restriction enzyme treatment of the intact cDNA or genomic DNA, which is used as a template in the site-directed mutagenesis, or by the PCR method using primers in which desired mutation has been introduced to obtain a DNA fragment in which the desired modification has been introduced. Thereafter, the mutated DNA fragment may be ligated to a DNA fragment encoding another portion of the enzyme of interest.

Alternatively, in order to obtain DNA encoding a protein comprising a shortened amino acid sequence, an amino acid sequence longer than the amino acid sequence of interest, for example, DNA encoding the full-length amino acid sequence, may be cleaved with a desired restriction enzyme, and when the resultant DNA fragment was found not to encode the entire amino acid sequence of interest, a DNA fragment comprising the sequence of the lacking portion may be synthesized and ligated thereto.

The present invention is not limited to a gene encoding a protein that has an activity of regulating the pH of vacuoles derived from morning glory, but the sources may be plants, animals, or microorganisms, and all they need is to have a topology that pumps protons out of the vacuole.

By expressing the obtained gene using a gene expression system in Escherichia coli or yeast and determining the activity, it can be confirmed that the gene obtained encodes a protein that has an activity of regulating the pH of vacuoles. Furthermore, by expressing said gene, a protein, the gene product, having an activity of regulating the pH of vacuoles can be obtained. Alternatively, a protein can also be obtained that has an activity of regulating the pH of vacuoles using an antibody against the amino acid sequence as set forth in SEQ ID NO: 2, and a protein that has an activity of regulating the pH of vacuoles derived from other organisms can be cloned using an antibody.

Thus, the present invention also relates to a recombinant vector comprising the above-mentioned gene, specifically an expression vector, and a host cell transformed with said vector. As a host, there can be used a prokaryotic or eukaryotic organism. As a prokaryotic organism, for example, there can be used such a common host as a bacterium belonging to the genus Escherichia such as Escherichia coli, a bacterium belonging to the genus Bacillus such as Bacillus subtilis, and the like. As a eukaryotic host, there can be used a lower eukaryotic organism, for example an eukaryotic microorganism such as a fungus, a yeast or a mold.

As yeast, there can be mentioned a microorganism belonging to the genus Saccharomyces such as Saccharomyces cerevisiae, and as a mold, there can be mentioned a microorganism belonging to the genus Aspergillus such as Aspergillus oryzae and Aspergillus niger, and a microorganism belonging to the genus Penicillium. Furthermore, animal cells or plant cells can be used: as animal cells, there can be used cell lines derived from mouse, hamster, monkey, human and the like. Insect cells such as silkworm cells or adult silkworms per se can also be used as hosts.

The vectors of the present invention may contain expression regulatory regions such as a promoter, a terminator, an origin of replication, and the like, depending on the type of the host into which said vector is to be introduced. As promoters for bacterial expression vectors, there can be used commonly used promoters such as trc promoter, tac promoter, lac promoter, and the like; as promoters for yeasts, there can be used the glyceraldehyde-3-phosphate dehydrogenase promoter, PHO5 promoter, and the like; and as mold promoters, there can be used amylase promoter, trpC promoter, and the like.

As promoters for animal cell hosts, there can be used viral promoters such as SV40 early promoter, SV40 late promoter, and the like. The construction of expression vectors may be performed according to conventional methods using restriction enzymes, ligase, etc. The transformation of host cells can also be performed according to conventional methods.

Host cells transformed with the above expression vectors may be cultured, cultivated or bred, and from the culture the desired protein can be recovered and purified according to conventional methods such as filtration, centrifugation, cell disruption, gel filtration chromatography, ion exchange chromatography, and the like.

The present invention also relates to a plant or its progenies or tissues thereof of which hue of color has been controlled by introducing a gene encoding a protein that has an activity of regulating the pH of the vacuoles, specifically a $Na^+$—$H^+$ antiporter gene. They may be cut flowers in shape. Using a gene encoding a protein that has an activity of regulating the pH of vacuoles obtained by the present invention, the pumping of proton into the cytoplasm from the vacuole and the pumping of sodium ion into the vacuole can be performed, so that anthocyanins accumulated in the vacuole can be turned blue and, as a result, the flower color can be turned blue.

It is also possible to lower the pH of vacuoles by suppressing the expression of the gene of the present invention. With the state-of-the-art technology, it is possible to introduce a gene into plants, and allow the gene to be expressed in a constitutive or tissue-specific manner, and also to suppress the expression of the gene of interest by the antisense method or the co-suppression method.

Examples of plants that can be transformed include, but not limited to, roses, chrysanthemums, carnations, snapdragons, cyclamens, orchids, lisianthus, freesias, gerberas, gladioluses, gypsophilas, kalanchoes, lilies, pelargoniumas, geraniums, petunias, torenias, tulips, rice, barley, whieat, rapeseeds, potatoes, tomatoes, poplars, bananas, eucalyptuses, sweet potatoes, soy beans, alfalfas, lupins, corns, and the like.

EXAMPLES

The present invention will now be explained in further details with reference to the following Examples. Molecular biological techniques used were performed according to Molecular Cloning (Sambrook et al., 1989), unless otherwise specified.

Example 1

Obtaining a Germ Cell Revertant

Obtaining a germ cell revertant has already been reported (Iida et al., Shokubutsu Saibo Kogaku Series (Plant Cell Engineering Series) 5 (1996) pp. 132, Shujunsha; Iida et al., Annal. New York Acad. Sci. (1999) pp. 870; Inagaki et al., Plant Cell, 6:375 (1994); Inagaki et al., Theor. Appl. Genet. 92:499 (1996)).

Morning glory having the genotype (Pr-r/pr-m) (Iida et al., pp. 870; Inagaki et al., Plant Cell, 6:375 (1994); Inagaki et al., Theor. Appl. Genet. 92:499 (1996)) was subjected to self-fertilization and the seeds of the progeny were planted. The flowers of the self-fertilized progeny were observed to select individuals that bloom with blue flowers by back mutation. Furthermore, in this self-fertilized progeny of the germ cell revertant, it was proved whether it is homozygous or heterozygous based on whether or not isolates that bloom with purple flowers can be obtained. Those having the genotype (Pr-r/Pr-r) and (pr-m/pr-m) were selected.

Example 2

Anthocyanins in the Petals of Revertants

Anthocyanins contained in morning glory are mainly heavenly blue anthocyanin and several other anthocyanins (Lu et al., Phytochemistry 31:659 (1992)). When the open petals of the Pr-r/Pr-r strain and the pr-m/pr-m strain obtained in Example 1 were similarly analyzed, the anthocyanins contained in both of them were almost identical.

A cellophane tape was stuck to the front side of a petal and then peeled off to recover one layer of epithelium, from which the cell liquid was scraped with a scalpel etc., which was then centrifuged to obtain juice. The pH of the juice was measured using the Horiba B212 pH meter (Horiba Seisakusho). pH of the petal epithelium of the Pr-r/Pr-r strain was about 7.1 whereas that of the pr-m/pr-m strain was about 6.5. This result indicates that the change in flower color by mutation of purple was not due to the structure of anthocyanins but to the change of vacuolar pH.

Example 3

Isolation of a Aenome Fragment Specifically Present in pr-m

For the isolation of a gene, the transposon display method (Frey et al., Plant J. 13:717 (1998); Van den Broeck et al., Plant J. 13:121 (1998)) or a similar method (Dosho et al., Shokubutsu Saibo Kogaku Series (Plant Cell Engineering Series) 7 (1997) pp. 144, Shujunsha) was used to search for DNA bands that were present in the pr-m/pr-m strain and the Pr-w/pr-m strain but not in the Pr-r/Pr-r strain or in the wild strain. Since Tpn1-related transposon is thought to be mainly associated with mutability in morning glory, special note was given to the Tpn1-related transposon.

Specifically, chromosomal DNA was extracted from the pr-m/pr-m strain, and 125 ng of it was digested with MseI in 20 μl. To the digested DNA was added 80 pmole of MseI adaptor (obtained by annealing 5'-GACGATGAGTCCTGAG-3' (SEQ ID NO: 3) and 5'-TACTCAGGACTCAT-3' (SEQ ID NO: 4)) in 25 μl at 20° C. for 2 hours. After keeping it at 75° C. for 10 minutes, it was stored at −20° C. After diluting this ten-fold, 2 μl was used as a template, which was PCR-amplified using 4.8 pmole of TIR primer (5'-TGTGCATTTTTCTTGTAGTG-3' (SEQ ID NO: 5), this includes the inverted terminal repeat of the transposon Tpnl) and 4.8 pmole of MseI primer (5'-GATGAGTCCTGAGTAA-3') (SEQ ID NO: 6) in 20 μl.

PCR was performed with Taq polymerase (Takara Shuzo) for 20 cycles with one cycle comprising 94° C. for 0.5 minute, 56° C. for 1 minute, and 72° C. for 1 minute, and the volume was diluted ten-fold. Two μl of it was used as a template in a PCR using 4.8 pmole of TIR+N primer (5'-TGTGCATTTTTCTTGTAGN-3' (SEQ ID NO: 7) N=A, C, G or T. Four different species were synthesized instead of a mixture) and 4.8 pmole of MseI+N primer (5'-GATGAGTCCTGAGTAAN-3' (SEQ ID NO: 8) N=A, C, G or T. Four different species were synthesized instead of a mixture. The 5'-end was labeled with fluorescein (using Amersham Pharmacia Biotek, Vistra fluorescence 5'-oligo labeling kit)) in 20 μl.

Reactions were performed for combinations of primers to a total of 16 reactions. PCR was performed for 13 cycles with one cycle comprising 94° C. for 0.5 minute, 65° C. (with a decrement of 0.7° C. for each cycle) for 1 minute, and 72° C. for 1 minute, and further for 13 cycles with one cycle comprising 94° C. for 0.5 minute, 56° C. for 1 minute, and 72° C. for 1 minute. A similar procedure was performed for chromosomal DNA obtained from the Pr-r/Pr-r strain, subjected to electrophoresis using a sequence gel of the DNA Sequencer 377 (PE Biosystems Japan), and the bands were detected using FMBIOII (Takara Shuzo).

When bands derived from the Pr-r/Pr-r strain and the pr-m/pr-m strain were compared, an about 130 bp DNA fragment was specifically expressed in the strain having pr-m. The 130 bp DNA fragment was recovered, and amplified by PCR (for 30 cycles with one cycle comprising 94° C. for 0.5 minute, 56° C. for 1 minute, and 72° C. for 1 minute) using 20 pmole TIR primer and 20 pmole MseI primer, which was then subcloned into the pGEM-T vector (Promega Corporation), and then the nucleotide sequence was determined. The sequence was 5'-TGAGCATTTTTCTTGTAGTG CTGAGATTTTCCTCCATTTGTCTGAAGCTCTTCATCCTTCAACAC TACCCCCACATCTCACCTTTCAAG GTCCAATCTTTATCATTCATCT TTACTCAGGACTCATCGTC-3' (SEQ ID NO: 9) (the single-underlined portion corresponds to a used primer, the double-underlined portion corresponds to an exon, and the rest corresponds to an intron). After the sequence as set forth in SEQ ID NO: 9 was used as a probe in Northern analysis, a transcription product of about 2.3 kb was found in the bud of morning glory having Pr-r, but a corresponding transcription product was not found in the pr-m/pr-m strain. Thus, it can be seen that this 2.3 kb transcription product corresponds to the Purple gene.

Example 4

Isolation of cDNA

About 6 million clones of a CDNA library (Inagaki et al., Plant Cell 6:375 (1994)) derived from the wild strain morning glory (Pr-w/Pr-w) were screened using the 130 bp DNA fragment as a probe, with a result that two positive clones were obtained. One of these clones had a 2237 bp CDNA, among which a 1626 bp-long open reading frame was observed (SEQ ID NO: 1). The predicted amino acid sequence had an identity of 29.3% and 73.4% with the $Na^+$—$H^+$ antiporter of yeast and Arabidopsis, respectively (Nhx1 and AtNhx1 , respectively, Gaxiola et al., Proc. Natl. Acad. Sci. USA 96:1480–1485 (1999)).

The result revealed that the Purple gene of morning glory encodes a $Na^+$—$H^+$ antiporter. Incidentally, although the $Na^+$—$H^+$ antiporter obtained from Arabidopsis is attracting attention as a protein that gives salt resistance to yeast, this is the first time that an association of the $Na^+$—$H^+$ antiporter with flower color was observed.

Example 5

Complementation Experiment of Yeast $Na^+$—$H^+$ Antiporter

The predicted amino acid sequence encoded by the Purple gene of morning glory has a homology with those of the $Na^+$—$H^+$ antiporters of yeast and Arabidopsis. Thus, in order to confirm whether the Purple gene product of morning glory can function as a $Na^+$—$H^+$ antiporter protein, a complementation experiment was performed using a yeast $Na^+$—$H^+$ antiporter mutant.

First, the following two DNA fragments were synthesized:

CBSC1-Linker (22 mer) 5'-CGA TAG ATC TGG GGG TCG ACA T-3' (SEQ ID NO: 12)

CSBD2-Linker (22 mer) 5'-CGA TGT CGA CCC CCA GAT CTA T-3' (SEQ ID NO: 13)

Figure 3:
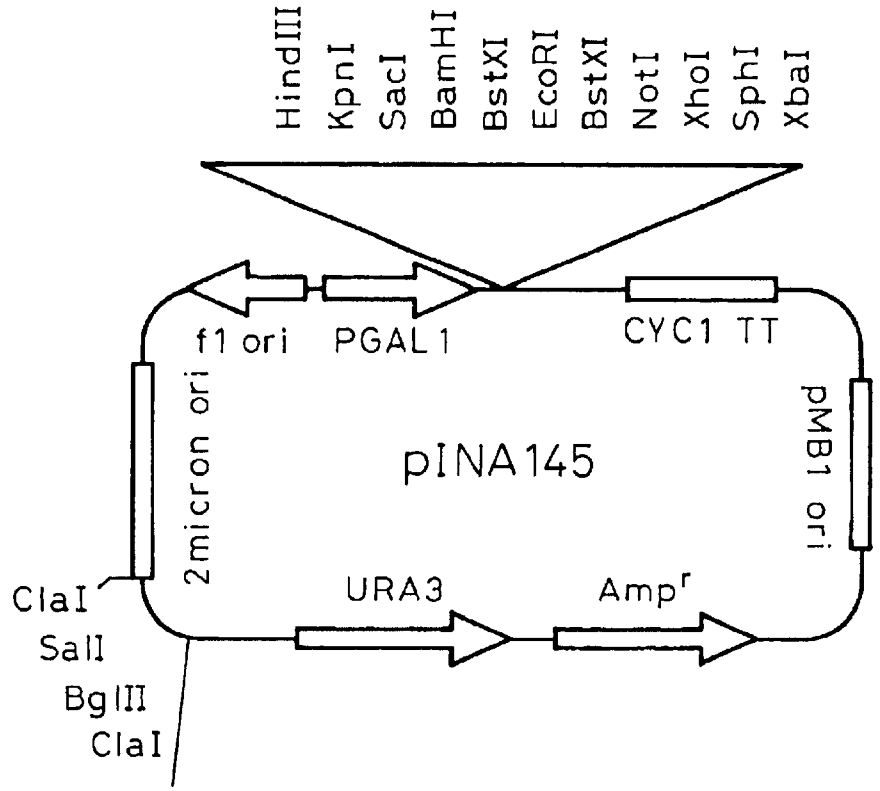
FIG. 3 is a drawing showing the structure of plasmid pINA145.
Figure 4:
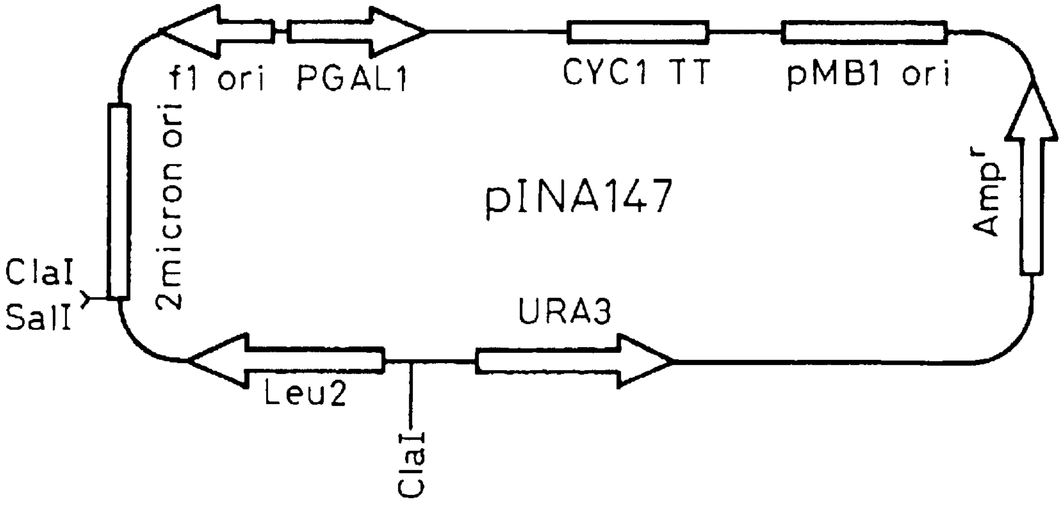
FIG. 4 is a drawing showing the structure of plasmid pINA147.

From these two fragments, a linker having restriction enzyme sites ClaI-BglII-SalI-ClaI is formed. A plasmid pINA145 (FIG. 3) was constructed by inserting the above linker according to a standard method into the ClaI site of the pYES2 vector (Invitrogen Corporation) so that the BglII site is located at the URA3 gene side. A plasmid pINA147 (FIG. 4) was constructed by ligating a 2 kb DNA fragment obtained by digesting plasmid pJJ250 (Jones and Prakash, Yeast 6:363–366 (1990)) with BamHI and SalI to plasmid pINA145 digested with BglII and SalI. Plasmid pIAN151 was constructed by ligating Purple cDNA thereto under the control of the GAL 1 promoter of plasmid pINA147. pINA147 and pIAN151 were transformed respectively to the yeast R101 strain which is a mutant strain of the $Na^+$—$H^+$ antiporter. Due to the mutation of the $Na^+$—$H^+$ antiporter, the yeast R101 strain cannot grow on a 400 mM NaCl-added APG medium (Nass et al., J. Biol. Chem. 272:26145 (1997); Gaxiola et al., 96:1480–1485 (1999)). The pINA147-transformed R101 strain could not grow either, and only the pIAN151-transformed R101 strain could grow on the 400 mM NaCl-added APG medium. The result has shown that the gene product of the morning glory Purple gene has the $Na^+$—$H^+$ antiporter function.

Example 6

Construction of an Expression Vector in Plants

With 10 ng of morning glory Purple cDNA as template, PCR was performed using synthetic primers PR-5 (5'-GGGATCCAACAAAAATGGCTGTCGGG-3') (SEQ ID NO: 10) and PR-3 (5'-GGGTCGACTAAGCATCAAAACATAGAGCC-3') (SEQ ID NO: 11). The polymerase used was Taq polymerase (Toyoboseki), and the reaction was performed, after reaction at 95° C. for 45 seconds, for 25 cycles with one cycle comprising 95° C. for 45 seconds, 50° C. for 45 seconds, and 72° C. for 45 seconds, and then further reacted at 72° C. for 10 minutes. An about 1.6 kb DNA fragment obtained was ligated to pCR2.1-Topo (Clontech) to make pCR-purple. It was confirmed that there were no errors due to PCR in the nucleotide sequence of Purple cDNA on this plasmid.

pBE2113-GUS (Mitsuhara et al., Plant Cell Physiol. 37:49 (1996)) was digested with SacI and blunt-ended. Then a XhoI linker (Toyoboseki) was inserted thereto, and the plasmid obtained was termed pBE2113-GUSx. This was digested with EcoRI and HindIII to obtain an about 2.7 kb DNA fragment, which was ligated to the HindIII and EcoRI digest of pBinPLUS, and the plasmid obtained was termed pBEXP.

On the other hand, an about 1.2 kb DNA fragment obtained by digesting pCGP484 (Kohyo (National Publication of Translated Version) No. 8-511683) with HindIII and XbaI, an about 1.6 kb DNA fragment obtained by digesting pCR-purple with XbaI and SalI, and an about 13 kb DNA fragment obtained by digesting pBEXP with HindIII and XhoI were ligated to obtain pSPB607 (FIG. 1). This plasmid is a binary vector for use in the Agrobacterium-mediated transformation of plants, and on this plasmid Purple cDNA is under the control of a chalcone synthase promoter derived from snapdragon and a nopaline synthase terminator derived from Agrobacterium.

Figure 2:
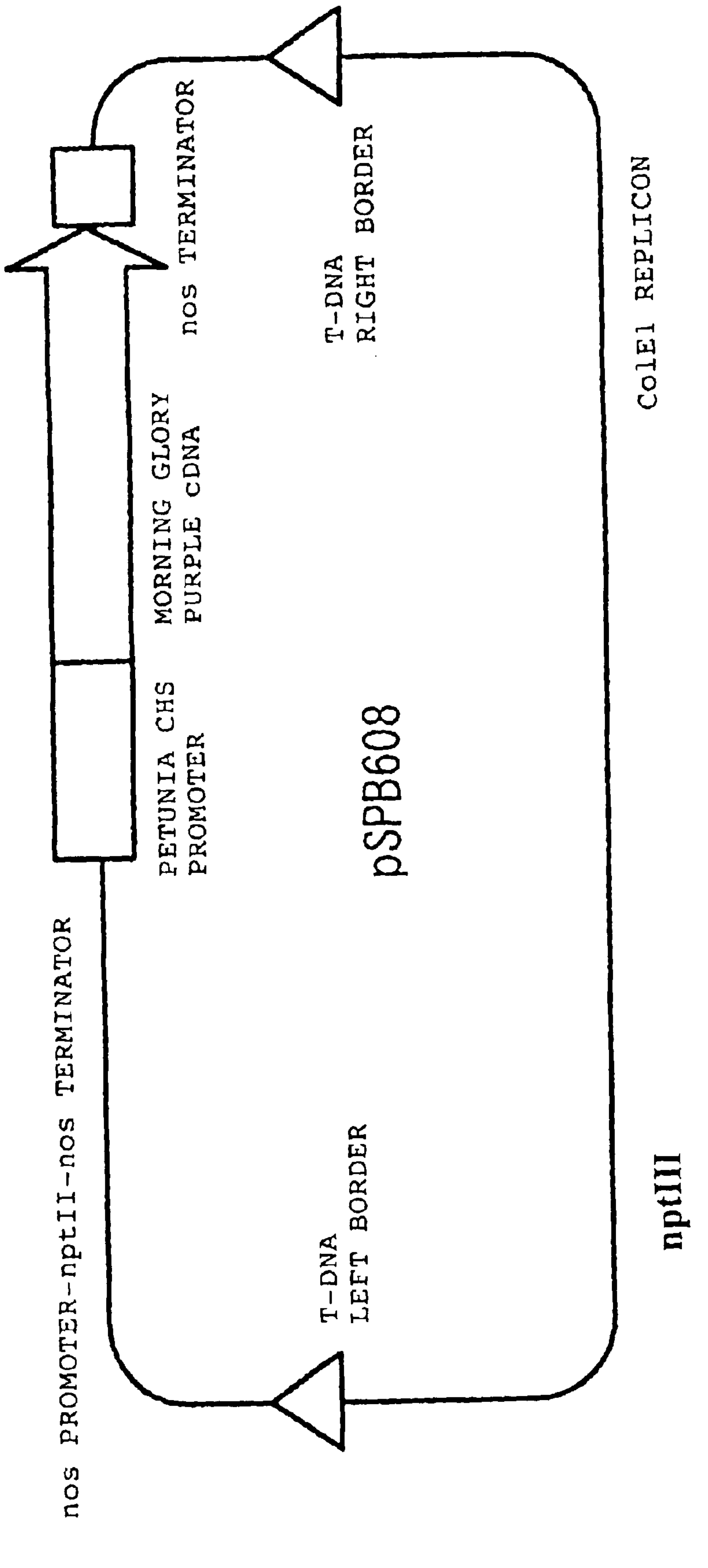
FIG. 2 is a drawing showing the structure of plasmid pSPB608.

An about 0.8 kb DNA fragment obtained by digesting pCGP669 (Kohyo (National Publication of Translated version) No. 8-511683) with HindIII and BamHI, an about 1.6 kb DNA fragment obtained by digesting pCR-purple with BamHI and SalI, and an about 13 kb DNA fragment obtained by digesting pBEXP with HindIII and XhoI were ligated to obtain pSPB608 (FIG. 2). This plasmid is a binary vector for use in the Agrobacterium-mediated transformation of plants, and on this plasmid Purple CDNA is under the control of a chalcone synthase promoter derived from petunia and a nopaline synthase terminator derived from Agrobacterium.

By transforming plants using the expression vectors thus obtained, the pH of vacuoles can be regulated and thereby flower color can be controlled.

Example 7

Isolation of a Homoloas of the Purple Gene cDNA libraries derived from the petals of petunia (Petunia hybrida cv. Old Glory Blue), Nierembergia (Nierembergia hybrida.cv. NB17), and Torenia (Torenia hybrida cv. Summerwave Blue) were each constructed using the cDNA synthesis kit (Stratagene, USA). The method of construction was as recommended by the manufacturer. About 200,000 clones each were screened according to a standard method. For washing the membrane, an aqueous solution of 5×SSC and 0.1% SDS was used and the incubation was performed three times at 50° C. for 10 minutes. Among the positive clones obtained, the nucleotide sequence of the longest clone was determined for each clone. The nucleotide sequence of the clone of Petunia and the corresponding amino acid sequence are shown in SEQ ID NO: 14 and 15, the nucleotide sequence of the clone of Nierembergia and the corresponding amino acid sequence are shown in SEQ ID NO: 16 and 17, and the nucleotide sequence of the clone of Torenia and the corresponding amino acid sequence are shown in SEQ ID NO: 18 and 19. Homologs of the Purple gene of Petunia, Nierembergia, and Torenia had an identity on the amino acid level of 75%, 76%, and 71%, respectively, with the morning glory Purple gene.

Since the amino acid sequence of the $Na^+$—$H^+$ antiporter encoded by the morning glory Purple gene and that of the $Na^+$—$H^+$ antiporter encoded by Arabidopsis AtNhx 1 are about 73% identical, the homologs of the Purple gene of Petunia, Nierembergia, and Torenia obtained are judged to encode the $Na^+$—$H^+$ antiporter.

Example 8

Isolation of the Clone of Mornina Glory Purple Chromosome

After chromosomal DNAs of a mutant morning glory (pr-m/pr-m) and a revertant morning glory (Pr-r/Pr-r) were cleaved with BglII, they were electrophoresed on a 0.8% agarose gel, and were subjected to genomic Southern analysis with cDNA of morning glory Purple as a probe. As a result, an about 7.5 kb band that was not present in the mutant morning glory was detected in the revertant morning glory.

After 50 μg of chromosomal DNA of the wild type morning glory (Pr-w/Pr-w, the KKZSK2 strain) was digested with BglII, it was electrophoresed on a 0.8% agarose gel. An about 7–9 kb fragmently was recovered, from which DNA was extracted using the GENECLEAN III KIT (B10101). This DNA was ligated to the λ Zap express vector (Stratagene, USA), which was screened with cDNA of morning glory Purple as a probe. The determination of nucleotide sequences of positive clones obtained revealed that, on this about 7.5 kb DNA fragment, there was a region from about 6.3 kb upstream of the Purple promoter to midway in exon 3. For this sequence, a sequence up to the initiation codon of the Purple gene is shown in SEQ ID NO: 20.

It has been demonstrated that the expression of the Purple gene is strongly induced only at about 24 hours before the flowering of morning glory, and that the expression of the Purple gene is suppressed by insertion of a transposon into the 5'-untranslated region. From this, it is clear that the promoter region of the Purple gene obtained contains a factor needed for the expression of the Purple gene in a developmental stage-specific and organ-specific manner in the petals of morning glory. By placing the gene of interest downstream of this promoter region, the expression of the gene of interest can be regulated in a developmental stage-specific and organ-specific manner.

Industrial Applicability

The gene obtained in the present invention was found, for the first time, to be involved in controlling the pH of vacuoles and flower color. By expressing the gene of the present invention on the flower petals, the pH of vacuoles can be increased and thereby the flower color can be turned blue. Furthermore, by suppressing the expression of the gene of the present invention, the pH of vacuoles can be lowered and thereby flower color can be turned red. As the gene encoding a protein that regulates the pH of vacuoles, there can be used not only those derived from morning glory obtained in the present invention but also similar genes derived from other organisms.

What is claimed is:

1. An isolated nucleic acid encoding a protein that has the amino acid sequence as set forth in SEQ ID NO: 2 and that has an activity of regulating the pH of vacuoles in plant cells.

2. A vector comprising the nucleic acid sequence according to claim 1.

3. A host cell transformed with the vector according to claim 2.

4. A transgenic plant in which the nucleic acid sequence according to claim 1 has been introduced or a progeny of said plant in which said nucleic acid sequence has been introduced in said progeny and in which the pH of vacuoles in the plant cells are regulated and flower color is altered, or a tissue thereof.

5. A cut flower of the plant according to claim 4 or a progeny of said plant in which said nucleic acid sequence has been introduced in said progeny and in which the pH of vacuoles in the plant cells are regulated and flower color is altered.

6. A method of regulating the pH of vacuoles comprising introducing the nucleic acid sequence according to claim 1 into a plant or plant cells and then allowing said nucleic acid sequence to be expressed in said plant or plant cells.

7. A method of controlling the flower color of a plant comprising introducing the nucleic acid sequence according to claim 1 into a plant or plant cells and then allowing said nucleic acid sequence to be expressed in said plant or plant cells.

* * * * *

UNITED STATES PATENT AND TRADEMARK OFFICE

CERTIFICATE OF CORRECTION

PATENT NO. : 6,803,500 B1
DATED : October 12, 2004
INVENTOR(S) : Shigeru Iida et al.

It is certified that error appears in the above-identified patent and that said Letters Patent is hereby corrected as shown below:

Title page,
Item [22], PCT Filing Date, change "Aug. 24, 1999" to -- Aug. 24, 2000 --.

Signed and Sealed this

Fifteenth Day of November, 2005

JON W. DUDAS
*Director of the United States Patent and Trademark Office*

SEQUENCE LISTING

```
<160> NUMBER OF SEQ ID NOS: 20

<210> SEQ ID NO 1
<211> LENGTH: 2237
<212> TYPE: DNA
<213> ORGANISM: Ipomoea nil
<220> FEATURE:
<221> NAME/KEY: misc_feature
<222> LOCATION: (1)..(2237)
<223> OTHER INFORMATION: Nucleotide sequence of DNA encoding for protein
      regulating the pH of vacuoles

<400> SEQUENCE: 1

agaatgtagg ctacagaaat tttcagacag atagatacat aaatccgtat aatagagaca     60

gagaaacaga aaaagagaga gtcacgttaa tcctgagatt ttcctccatt tgtctgaagc    120

tcttcatcct tcaacactac ccccacatct cacctttcaa gtgatttgta tgttttcggg    180

agggattgga atgggcaacc cggatatgtg aacagaaacc acgacattgg gaaaagattt    240

attgcaaaaa ttgttttgat tgttttggat tttgtggtag aaaaagggga agaacaaaa     299

atg gcg ttc ggg ttg tct tct ttg ctc caa aat tcg gat ttg ttc acg      347
Met Ala Phe Gly Leu Ser Ser Leu Leu Gln Asn Ser Asp Leu Phe Thr
  1               5                  10                  15

tct gat cat gct tcc gtt gtg tcg atg aac ctc ttt gtg gcg ttg ctt      395
Ser Asp His Ala Ser Val Val Ser Met Asn Leu Phe Val Ala Leu Leu
             20                  25                  30

tgc gca tgc att gtt ctt ggc cat cta ctc gag gag aat cgc tgg gtg      443
Cys Ala Cys Ile Val Leu Gly His Leu Leu Glu Glu Asn Arg Trp Val
         35                  40                  45

aac gaa tcc att act gcc ctt ata att ggt ttg tgc acc gga gtt gta      491
Asn Glu Ser Ile Thr Ala Leu Ile Ile Gly Leu Cys Thr Gly Val Val
     50                  55                  60

att ttg ctc ctt agc gga gga aag agt tca cat ctt ctc gtc ttt agc      539
Ile Leu Leu Leu Ser Gly Gly Lys Ser Ser His Leu Leu Val Phe Ser
 65                  70                  75                  80

gaa gat ctt ttc ttt ata tat ctc ctg cca cct ata ata ttc aat gcg      587
Glu Asp Leu Phe Phe Ile Tyr Leu Leu Pro Pro Ile Ile Phe Asn Ala
                 85                  90                  95

ggg ttt caa gtg aaa aag aag cag ttt ttc gtg aac ttc atg aca att      635
Gly Phe Gln Val Lys Lys Lys Gln Phe Phe Val Asn Phe Met Thr Ile
            100                 105                 110

atg ctg ttt gga gct att ggc aca ctt att agc tgt tct att ata tca      683
Met Leu Phe Gly Ala Ile Gly Thr Leu Ile Ser Cys Ser Ile Ile Ser
        115                 120                 125

ttt ggt gcg gtc aaa att ttc aag cac tta gac att gac ttt ctg gat      731
Phe Gly Ala Val Lys Ile Phe Lys His Leu Asp Ile Asp Phe Leu Asp
    130                 135                 140
```

-continued

```
ttt gga gat tat tta gca att ggt gcg ata ttt gct gca acc gat tct      779
Phe Gly Asp Tyr Leu Ala Ile Gly Ala Ile Phe Ala Ala Thr Asp Ser
145                 150                 155                 160

gtt tgc aca ttg cag gtg ctc agt cag gat gag acg ccc cta ctt tac      827
Val Cys Thr Leu Gln Val Leu Ser Gln Asp Glu Thr Pro Leu Leu Tyr
                165                 170                 175

agt ctc gtg ttt gga gaa ggg gtc gtc aat gat gct aca tct gtg gtc      875
Ser Leu Val Phe Gly Glu Gly Val Val Asn Asp Ala Thr Ser Val Val
            180                 185                 190

ctt ttt aat gct att caa agt ttt gac atg act agt ttt gat cca aaa      923
Leu Phe Asn Ala Ile Gln Ser Phe Asp Met Thr Ser Phe Asp Pro Lys
        195                 200                 205

att ggg ctt cat ttc att gga aac ttc ttg tat tta ttt ctc tcg agc      971
Ile Gly Leu His Phe Ile Gly Asn Phe Leu Tyr Leu Phe Leu Ser Ser
    210                 215                 220

act ttt ttg ggc gtg gga att gga ctg ctt tgt gct tat att atc aaa     1019
Thr Phe Leu Gly Val Gly Ile Gly Leu Leu Cys Ala Tyr Ile Ile Lys
225                 230                 235                 240

aag cta tac ttt ggc agg cac tca acc gat cgt gag gtt gcc ctt atg     1067
Lys Leu Tyr Phe Gly Arg His Ser Thr Asp Arg Glu Val Ala Leu Met
                245                 250                 255

atg ctc atg tct tac ttg tct tat ata atg gcc gag tta ttc tat cta     1115
Met Leu Met Ser Tyr Leu Ser Tyr Ile Met Ala Glu Leu Phe Tyr Leu
            260                 265                 270

agc ggc ata ctt act gta ttc ttc tgt gga att gtc atg tct cat tat     1163
Ser Gly Ile Leu Thr Val Phe Phe Cys Gly Ile Val Met Ser His Tyr
        275                 280                 285

acc tgg cac aat gtt acc gag agc tca agg gtc act act agg cat tcc     1211
Thr Trp His Asn Val Thr Glu Ser Ser Arg Val Thr Thr Arg His Ser
    290                 295                 300

ttt gca act ctg tca ttt gtc gca gag aca ttt atc ttc ctc tat gtt     1259
Phe Ala Thr Leu Ser Phe Val Ala Glu Thr Phe Ile Phe Leu Tyr Val
305                 310                 315                 320

ggt atg gat gcc ttg gat atc gag aaa tgg aaa ttt gtg aaa aat agt     1307
Gly Met Asp Ala Leu Asp Ile Glu Lys Trp Lys Phe Val Lys Asn Ser
                325                 330                 335

cag gga cta tca gtt gca gtg agc tca ata ttg gta ggc cta atc tta     1355
Gln Gly Leu Ser Val Ala Val Ser Ser Ile Leu Val Gly Leu Ile Leu
            340                 345                 350

gta ggc aga gct gcg ttc gta ttc ccc ttg tcg ttt tta tcc aac tta     1403
Val Gly Arg Ala Ala Phe Val Phe Pro Leu Ser Phe Leu Ser Asn Leu
        355                 360                 365

gca aag aaa aac tct tcg gac aag ata tcc ttt agg caa caa ata ata     1451
Ala Lys Lys Asn Ser Ser Asp Lys Ile Ser Phe Arg Gln Gln Ile Ile
    370                 375                 380

att tgg tgg gct ggc cta atg aga ggc gcc gtc tca ata gca ctt gcg     1499
Ile Trp Trp Ala Gly Leu Met Arg Gly Ala Val Ser Ile Ala Leu Ala
385                 390                 395                 400

tat aat aag ttt aca acc tcg ggg cat acg tca ttg cac gag aac gca     1547
Tyr Asn Lys Phe Thr Thr Ser Gly His Thr Ser Leu His Glu Asn Ala
                405                 410                 415

ata atg att aca agt act gtt acg gtt gtt ctg ttc agc aca gtt gta     1595
Ile Met Ile Thr Ser Thr Val Thr Val Val Leu Phe Ser Thr Val Val
            420                 425                 430

ttc ggg ttg atg acg aag cct ctg ata aac ctt ctg cta ccc ccg cac     1643
Phe Gly Leu Met Thr Lys Pro Leu Ile Asn Leu Leu Leu Pro Pro His
        435                 440                 445

aag cag atg cca agc ggt cat tcg tca atg aca aca tcc gaa ccc agt     1691
Lys Gln Met Pro Ser Gly His Ser Ser Met Thr Thr Ser Glu Pro Ser
    450                 455                 460
```

-continued agt ccg aag cac ttc acg gtg cca ctc ctg gac aac caa cct gac tca 1739
Ser Pro Lys His Phe Thr Val Pro Leu Leu Asp Asn Gln Pro Asp Ser
465 470 475 480 gaa agc gat atg ata acc gga cct gag gtt gct cga cca act gcc ttg 1787
Glu Ser Asp Met Ile Thr Gly Pro Glu Val Ala Arg Pro Thr Ala Leu
485 490 495 cgc atg ctg cta agg acg cca acc cac acc gtg cac cgc tac tgg cgt 1835
Arg Met Leu Leu Arg Thr Pro Thr His Thr Val His Arg Tyr Trp Arg
500 505 510 aag ttt gat gat tcg ttt atg cgt ccc gtg ttt ggc ggg cgg gga ttc 1883
Lys Phe Asp Asp Ser Phe Met Arg Pro Val Phe Gly Gly Arg Gly Phe
515 520 525 gtt ccg ttt gtc gcg ggc tca cca gtt gag cag agc cct aga tga 1928
Val Pro Phe Val Ala Gly Ser Pro Val Glu Gln Ser Pro Arg
530 535 540 ggtacaaagt acaaacaaga cactgttgct gggtgaaata gtgtaagttg tatcatagtt 1988 gattctggtt gcccctctta tgaaatgggc tgggtgaaag tcttctcact agctaggttg 2048 cattgcattg ctacttcata aatgttttat tttattttgt aaatgttggt gcattttagg 2108 tacttgtatt aacacctcat ttgtagcata ttatttggta cagagtattt tttttatgaa 2168 acaataatgg ctgaattatc aatttggctc tatgttttga tgcttagtaa aaaaaaaaaa 2228 aaaaaaaaa 2237

<210> SEQ ID NO 2
<211> LENGTH: 542
<212> TYPE: PRT
<213> ORGANISM: Ipomea nil
<220> FEATURE:
<221> NAME/KEY: peptide
<222> LOCATION: (1)..(542)
<223> OTHER INFORMATION: Amino acid sequence of protein regulating the pH of vacuoles

<400> SEQUENCE: 2

Met Ala Phe Gly Leu Ser Ser Leu Leu Gln Asn Ser Asp Leu Phe Thr
1 5 10 15

Ser Asp His Ala Ser Val Val Ser Met Asn Leu Phe Val Ala Leu Leu
20 25 30

Cys Ala Cys Ile Val Leu Gly His Leu Leu Glu Glu Asn Arg Trp Val
35 40 45

Asn Glu Ser Ile Thr Ala Leu Ile Ile Gly Leu Cys Thr Gly Val Val
50 55 60

Ile Leu Leu Leu Ser Gly Gly Lys Ser Ser His Leu Leu Val Phe Ser
65 70 75 80

Glu Asp Leu Phe Phe Ile Tyr Leu Leu Pro Pro Ile Ile Phe Asn Ala
85 90 95

Gly Phe Gln Val Lys Lys Lys Gln Phe Phe Val Asn Phe Met Thr Ile
100 105 110

Met Leu Phe Gly Ala Ile Gly Thr Leu Ile Ser Cys Ser Ile Ile Ser
115 120 125

Phe Gly Ala Val Lys Ile Phe Lys His Leu Asp Ile Asp Phe Leu Asp
130 135 140

Phe Gly Asp Tyr Leu Ala Ile Gly Ala Ile Phe Ala Ala Thr Asp Ser
145 150 155 160

Val Cys Thr Leu Gln Val Leu Ser Gln Asp Glu Thr Pro Leu Leu Tyr
165 170 175

-continued

```
Ser Leu Val Phe Gly Glu Gly Val Val Asn Asp Ala Thr Ser Val Val
            180                 185                 190

Leu Phe Asn Ala Ile Gln Ser Phe Asp Met Thr Ser Phe Asp Pro Lys
        195                 200                 205

Ile Gly Leu His Phe Ile Gly Asn Phe Leu Tyr Leu Phe Leu Ser Ser
    210                 215                 220

Thr Phe Leu Gly Val Gly Ile Gly Leu Leu Cys Ala Tyr Ile Ile Lys
225                 230                 235                 240

Lys Leu Tyr Phe Gly Arg His Ser Thr Asp Arg Glu Val Ala Leu Met
                245                 250                 255

Met Leu Met Ser Tyr Leu Ser Tyr Ile Met Ala Glu Leu Phe Tyr Leu
            260                 265                 270

Ser Gly Ile Leu Thr Val Phe Phe Cys Gly Ile Val Met Ser His Tyr
        275                 280                 285

Thr Trp His Asn Val Thr Glu Ser Ser Arg Val Thr Thr Arg His Ser
    290                 295                 300

Phe Ala Thr Leu Ser Phe Val Ala Glu Thr Phe Ile Phe Leu Tyr Val
305                 310                 315                 320

Gly Met Asp Ala Leu Asp Ile Glu Lys Trp Lys Phe Val Lys Asn Ser
                325                 330                 335

Gln Gly Leu Ser Val Ala Val Ser Ser Ile Leu Val Gly Leu Ile Leu
            340                 345                 350

Val Gly Arg Ala Ala Phe Val Phe Pro Leu Ser Phe Leu Ser Asn Leu
        355                 360                 365

Ala Lys Lys Asn Ser Ser Asp Lys Ile Ser Phe Arg Gln Gln Ile Ile
    370                 375                 380

Ile Trp Trp Ala Gly Leu Met Arg Gly Ala Val Ser Ile Ala Leu Ala
385                 390                 395                 400

Tyr Asn Lys Phe Thr Thr Ser Gly His Thr Ser Leu His Glu Asn Ala
                405                 410                 415

Ile Met Ile Thr Ser Thr Val Thr Val Val Leu Phe Ser Thr Val Val
            420                 425                 430

Phe Gly Leu Met Thr Lys Pro Leu Ile Asn Leu Leu Leu Pro Pro His
        435                 440                 445

Lys Gln Met Pro Ser Gly His Ser Ser Met Thr Thr Ser Glu Pro Ser
    450                 455                 460

Ser Pro Lys His Phe Thr Val Pro Leu Leu Asp Asn Gln Pro Asp Ser
465                 470                 475                 480

Glu Ser Asp Met Ile Thr Gly Pro Glu Val Ala Arg Pro Thr Ala Leu
                485                 490                 495

Arg Met Leu Leu Arg Thr Pro Thr His Thr Val His Arg Tyr Trp Arg
            500                 505                 510

Lys Phe Asp Asp Ser Phe Met Arg Pro Val Phe Gly Gly Arg Gly Phe
        515                 520                 525

Val Pro Phe Val Ala Gly Ser Pro Val Glu Gln Ser Pro Arg
    530                 535                 540
```

<210> SEQ ID NO 3
<211> LENGTH: 16
<212> TYPE: DNA
<213> ORGANISM: Artificial Sequence
<220> FEATURE:
<223> OTHER INFORMATION: MseI adaptor

<400> SEQUENCE: 3

-continued

```
gacgatgagt cctgag                                                    16


<210> SEQ ID NO 4
<211> LENGTH: 14
<212> TYPE: DNA
<213> ORGANISM: Artificial Sequence
<220> FEATURE:
<223> OTHER INFORMATION: MseI adaptor

<400> SEQUENCE: 4

tactcaggac tcat                                                      14


<210> SEQ ID NO 5
<211> LENGTH: 20
<212> TYPE: DNA
<213> ORGANISM: Artificial Sequence
<220> FEATURE:
<223> OTHER INFORMATION: TIR primer

<400> SEQUENCE: 5

tgtgcatttt tcttgtagtg                                                20


<210> SEQ ID NO 6
<211> LENGTH: 16
<212> TYPE: DNA
<213> ORGANISM: Artificial Sequence
<220> FEATURE:
<223> OTHER INFORMATION: MseI primer

<400> SEQUENCE: 6

gatgagtcct gagtaa                                                    16


<210> SEQ ID NO 7
<211> LENGTH: 19
<212> TYPE: DNA
<213> ORGANISM: Artificial Sequence
<220> FEATURE:
<223> OTHER INFORMATION: TIR+N primer
<221> NAME/KEY: misc_feature
<222> LOCATION: (19)..(19)
<223> OTHER INFORMATION: Nucleotide 19 = “n” wherein “n” = any
      nucleotide

<400> SEQUENCE: 7

tgtgcatttt tcttgtagn                                                 19


<210> SEQ ID NO 8
<211> LENGTH: 17
<212> TYPE: DNA
<213> ORGANISM: Artificial Sequence
<220> FEATURE:
<223> OTHER INFORMATION: MseI+N primer
<221> NAME/KEY: misc_feature
<222> LOCATION: (17)..(17)
<223> OTHER INFORMATION: Nucleotide 17 = “n” wherein “n” = any
      nucleotide

<400> SEQUENCE: 8

gatgagtcct gagtaan                                                   17


<210> SEQ ID NO 9
<211> LENGTH: 130
<212> TYPE: DNA
<213> ORGANISM: Artificial Sequence
<220> FEATURE:
<223> OTHER INFORMATION: MseI+N primer

<400> SEQUENCE: 9
```

-continued

```
tgagcatttt tcttgtagtg ctgagatttt cctccatttg tctgaagctc ttcatccttc     60

aacactaccc ccacatctca cctttcaagg tccaatcttt atcattcatc tttactcagg    120

actcatcgtc                                                           130


<210> SEQ ID NO 10
<211> LENGTH: 26
<212> TYPE: DNA
<213> ORGANISM: Artificial Sequence
<220> FEATURE:
<223> OTHER INFORMATION: PR-5 primer

<400> SEQUENCE: 10

gggatccaac aaaaatggct gtcggg                                          26


<210> SEQ ID NO 11
<211> LENGTH: 29
<212> TYPE: DNA
<213> ORGANISM: Artificial Sequence
<220> FEATURE:
<223> OTHER INFORMATION: PR-3 primer

<400> SEQUENCE: 11

gggtcgacta agcatcaaaa catagagcc                                       29


<210> SEQ ID NO 12
<211> LENGTH: 22
<212> TYPE: DNA
<213> ORGANISM: Artificial Sequence
<220> FEATURE:
<223> OTHER INFORMATION: CBSC1-linker

<400> SEQUENCE: 12

cgatagatct gggggtcgac at                                              22


<210> SEQ ID NO 13
<211> LENGTH: 22
<212> TYPE: DNA
<213> ORGANISM: Artificial Sequence
<220> FEATURE:
<223> OTHER INFORMATION: CBSC2-linker

<400> SEQUENCE: 13

cgatgtcgac ccccagatct at                                              22


<210> SEQ ID NO 14
<211> LENGTH: 2423
<212> TYPE: DNA
<213> ORGANISM: Petunia hybrida
<220> FEATURE:
<221> NAME/KEY: misc_feature
<222> LOCATION: (1)..(2423)
<223> OTHER INFORMATION: Nucleotide sequence of DNA encoding for protein
      regulating the pH of vacuoles

<400> SEQUENCE: 14

attgcgcttc gtattttact gctgaatgaa atcgtgtttt tttattcagt tcgttgttat     60

taatttcaga gttttttta ttaaaggtgt gtttggttga agaaattgta tttgctgaat    120

tttgcagaag tttttgagtt tttgctaaac tattgtgaga tctgattttg aatttttcca    180

gtggtgtttt aagctcaatt cgacgtcgtt tttactggaa ttctgatcag taaatagggc    240

tattttgatg taaggttgtg aaagtttaca gtttggaagt tgagttagtg aaaaagggga    300

aactttattg tgatattttc acaagtattt ggtgaattca ggttattgag a atg gct     357
```

-continued

```
                                                Met Ala

ttt gat ttt ggg acg ttg ttg gga aat gta gac agg tta tcg aca tct      405
Phe Asp Phe Gly Thr Leu Leu Gly Asn Val Asp Arg Leu Ser Thr Ser
          5                  10                  15

gat cat caa tca gtt gtg tcg ata aac tta ttc gtt gct ctt att tgc      453
Asp His Gln Ser Val Val Ser Ile Asn Leu Phe Val Ala Leu Ile Cys
     20                  25                  30

gcg tgt att gtg atc ggt cat ttg ttg gaa gaa aac aga tgg atg aat      501
Ala Cys Ile Val Ile Gly His Leu Leu Glu Glu Asn Arg Trp Met Asn
 35                  40                  45                  50

gag tcc ata act gcc tta gtg att ggt tct tgt act gga atc gtt att      549
Glu Ser Ile Thr Ala Leu Val Ile Gly Ser Cys Thr Gly Ile Val Ile
                 55                  60                  65

cta ctg ata agt gga gga aag aac tct cat att tta gtg ttc agt gaa      597
Leu Leu Ile Ser Gly Gly Lys Asn Ser His Ile Leu Val Phe Ser Glu
             70                  75                  80

gat ctt ttc ttc att tac ctt ctt ccg cca atc att ttt aat gct ggg      645
Asp Leu Phe Phe Ile Tyr Leu Leu Pro Pro Ile Ile Phe Asn Ala Gly
         85                  90                  95

ttc cag gtg aaa aag aaa tcg ttc ttc cgc aat ttc agc act atc atg      693
Phe Gln Val Lys Lys Lys Ser Phe Phe Arg Asn Phe Ser Thr Ile Met
    100                 105                 110

ctc ttt ggg gca ctt ggc acc ttg ata tca ttc att att ata tca tta      741
Leu Phe Gly Ala Leu Gly Thr Leu Ile Ser Phe Ile Ile Ile Ser Leu
115                 120                 125                 130

ggt gcc att ggc att ttc aag aaa atg aat att gga agc ctt gaa att      789
Gly Ala Ile Gly Ile Phe Lys Lys Met Asn Ile Gly Ser Leu Glu Ile
                135                 140                 145

gga gat tac ctt gca att ggg gca atc ttc tct gct aca gat tct gta      837
Gly Asp Tyr Leu Ala Ile Gly Ala Ile Phe Ser Ala Thr Asp Ser Val
            150                 155                 160

tgc acc tta caa gtg ctt aat cag gat gaa aca ccc tta ttg tac agt      885
Cys Thr Leu Gln Val Leu Asn Gln Asp Glu Thr Pro Leu Leu Tyr Ser
        165                 170                 175

cta gtt ttt ggg gaa ggt gtt gtg aat gat gcc aca tct gta gtt ctg      933
Leu Val Phe Gly Glu Gly Val Val Asn Asp Ala Thr Ser Val Val Leu
    180                 185                 190

ttc aat gct atc cag aac ttt gac tta tct cac atc gac acg ggc aaa      981
Phe Asn Ala Ile Gln Asn Phe Asp Leu Ser His Ile Asp Thr Gly Lys
195                 200                 205                 210

gct atg gaa tta gtt gga aac ttt cta tac ttg ttt gcc tca agc act     1029
Ala Met Glu Leu Val Gly Asn Phe Leu Tyr Leu Phe Ala Ser Ser Thr
                215                 220                 225

gcc cta gga gtt gct gct ggc cta ctg agc gcc tat att att aaa aaa     1077
Ala Leu Gly Val Ala Ala Gly Leu Leu Ser Ala Tyr Ile Ile Lys Lys
            230                 235                 240

ctc tac ttt gga agg cac tca act gac cgt gag gtt gct ata atg ata     1125
Leu Tyr Phe Gly Arg His Ser Thr Asp Arg Glu Val Ala Ile Met Ile
        245                 250                 255

ctc atg gct tac cta tct tac atg ctt gct gaa tta ttc tat tta agt     1173
Leu Met Ala Tyr Leu Ser Tyr Met Leu Ala Glu Leu Phe Tyr Leu Ser
    260                 265                 270

gca atc ctc act gtg ttt ttc tct ggg atc gtg atg tct cac tac acc     1221
Ala Ile Leu Thr Val Phe Phe Ser Gly Ile Val Met Ser His Tyr Thr
275                 280                 285                 290

tgg cat aat gtg act gag agc tcg aga gtc act acc aag cac act ttt     1269
Trp His Asn Val Thr Glu Ser Ser Arg Val Thr Thr Lys His Thr Phe
                295                 300                 305

gct aca tta tca ttt att gct gaa ata ttc ata ttc ctt tat gtt ggt     1317
```

```
                Ala Thr Leu Ser Phe Ile Ala Glu Ile Phe Ile Phe Leu Tyr Val Gly
                            310                 315                 320

atg gat gct ttg gac att gag aag tgg aag ttt gta agc gac agc cct          1365
Met Asp Ala Leu Asp Ile Glu Lys Trp Lys Phe Val Ser Asp Ser Pro
                325                 330                 335

gga ata tca gtt cag gtt agc tca ata ttg ctg ggt ctt gtt ttg gtt          1413
Gly Ile Ser Val Gln Val Ser Ser Ile Leu Leu Gly Leu Val Leu Val
            340                 345                 350

gga aga gca gca ttt gtt ttc cca ttg tca ttc ttg tcc aac ttg acc          1461
Gly Arg Ala Ala Phe Val Phe Pro Leu Ser Phe Leu Ser Asn Leu Thr
355                 360                 365                 370

aag aaa act cca gag gcg aaa att agt ttt aac cag cag gtt aca ata          1509
Lys Lys Thr Pro Glu Ala Lys Ile Ser Phe Asn Gln Gln Val Thr Ile
                375                 380                 385

tgg tgg gct gga ctt atg aga ggt gcc gtt tct atg gcc ctt gct tat          1557
Trp Trp Ala Gly Leu Met Arg Gly Ala Val Ser Met Ala Leu Ala Tyr
            390                 395                 400

aat cag ttt acc agg gga ggt cat act cag tta cgc gca aat gca ata          1605
Asn Gln Phe Thr Arg Gly Gly His Thr Gln Leu Arg Ala Asn Ala Ile
            405                 410                 415

atg atc aca agt act atc act gtt gtc ctt ttc agc aca gtc gtg ttt          1653
Met Ile Thr Ser Thr Ile Thr Val Val Leu Phe Ser Thr Val Val Phe
        420                 425                 430

ggg ttg atg aca aaa cct ttg att aga ata ttg cta ccc tca cac aaa          1701
Gly Leu Met Thr Lys Pro Leu Ile Arg Ile Leu Leu Pro Ser His Lys
435                 440                 445                 450

cac ttg agc aga atg atc tct tct gaa cca acg acc cca aaa tcc ttc          1749
His Leu Ser Arg Met Ile Ser Ser Glu Pro Thr Thr Pro Lys Ser Phe
                455                 460                 465

att gtg cca ctt ctt gac agc aca caa gac tca gaa gct gat ctg gaa          1797
Ile Val Pro Leu Leu Asp Ser Thr Gln Asp Ser Glu Ala Asp Leu Glu
            470                 475                 480

cgc cat gta ccc cgt ccc cac agt ttg cgg atg ctc ctt tca acc cca          1845
Arg His Val Pro Arg Pro His Ser Leu Arg Met Leu Leu Ser Thr Pro
            485                 490                 495

tct cat aca gtg cat tat tac tgg aga aag ttt gac aat gca ttc atg          1893
Ser His Thr Val His Tyr Tyr Trp Arg Lys Phe Asp Asn Ala Phe Met
        500                 505                 510

cgt cca gtt ttc ggt gga cga ggt ttt gta cct ttt gct cca gga tca          1941
Arg Pro Val Phe Gly Gly Arg Gly Phe Val Pro Phe Ala Pro Gly Ser
515                 520                 525                 530

ccg aca gac cca gtt ggt gga aat ttg caa tgatggagat acagattgca           1991
Pro Thr Asp Pro Val Gly Gly Asn Leu Gln
                535                 540

aaaagtggtc ttggtgaggg aagagggcag ttttttggta atgaggttcc gttttcttta      2051

atgttaatag caagtgtggt taaaaagggg ttgtctagtt tataggtttt gcagatctca      2111

agtatattca tttgggtgat catgttttca gctcagttat tgcttttggt cattgctgac      2171

catcaatttc tgtggggaat tcctataggt tttctcccta acagttcttt tcttcatctt      2231

tttgcaattt atcgaaacac caaatgggtg tatattctgt aagcttgtgg catagctagc      2291

ttaattgtct tgtaaaattt cctacaggtt agagattggt tcttgatatg tagatttcat      2351

atgattgtaa cattcccatt tctcagaaaa gaaactataa tataaaattt ctggtggctg      2411

tcgcccgtgc tc                                                           2423

<210> SEQ ID NO 15
<211> LENGTH: 540
<212> TYPE: PRT
```

-continued

```
<213> ORGANISM: Petunia hybrida
<220> FEATURE:
<221> NAME/KEY: peptide
<222> LOCATION: (1)..(540)
<223> OTHER INFORMATION: Amino acid sequence of protein regulating the
      pH of vacuoles

<400> SEQUENCE: 15

Met Ala Phe Asp Phe Gly Thr Leu Leu Gly Asn Val Asp Arg Leu Ser
                5                   10                  15

Thr Ser Asp His Gln Ser Val Val Ser Ile Asn Leu Phe Val Ala Leu
            20                  25                  30

Ile Cys Ala Cys Ile Val Ile Gly His Leu Leu Glu Glu Asn Arg Trp
        35                  40                  45

Met Asn Glu Ser Ile Thr Ala Leu Val Ile Gly Ser Cys Thr Gly Ile
    50                  55                  60

Val Ile Leu Leu Ile Ser Gly Gly Lys Asn Ser His Ile Leu Val Phe
65                  70                  75                  80

Ser Glu Asp Leu Phe Phe Ile Tyr Leu Leu Pro Pro Ile Ile Phe Asn
                85                  90                  95

Ala Gly Phe Gln Val Lys Lys Lys Ser Phe Phe Arg Asn Phe Ser Thr
            100                 105                 110

Ile Met Leu Phe Gly Ala Leu Gly Thr Leu Ile Ser Phe Ile Ile Ile
        115                 120                 125

Ser Leu Gly Ala Ile Gly Ile Phe Lys Lys Met Asn Ile Gly Ser Leu
    130                 135                 140

Glu Ile Gly Asp Tyr Leu Ala Ile Gly Ala Ile Phe Ser Ala Thr Asp
145                 150                 155                 160

Ser Val Cys Thr Leu Gln Val Leu Asn Gln Asp Glu Thr Pro Leu Leu
                165                 170                 175

Tyr Ser Leu Val Phe Gly Glu Gly Val Val Asn Asp Ala Thr Ser Val
            180                 185                 190

Val Leu Phe Asn Ala Ile Gln Asn Phe Asp Leu Ser His Ile Asp Thr
        195                 200                 205

Gly Lys Ala Met Glu Leu Val Gly Asn Phe Leu Tyr Leu Phe Ala Ser
    210                 215                 220

Ser Thr Ala Leu Gly Val Ala Ala Gly Leu Leu Ser Ala Tyr Ile Ile
225                 230                 235                 240

Lys Lys Leu Tyr Phe Gly Arg His Ser Thr Asp Arg Glu Val Ala Ile
                245                 250                 255

Met Ile Leu Met Ala Tyr Leu Ser Tyr Met Leu Ala Glu Leu Phe Tyr
            260                 265                 270

Leu Ser Ala Ile Leu Thr Val Phe Phe Ser Gly Ile Val Met Ser His
        275                 280                 285

Tyr Thr Trp His Asn Val Thr Glu Ser Ser Arg Val Thr Thr Lys His
    290                 295                 300

Thr Phe Ala Thr Leu Ser Phe Ile Ala Glu Ile Phe Ile Phe Leu Tyr
305                310                 315                 320

Val Gly Met Asp Ala Leu Asp Ile Glu Lys Trp Lys Phe Val Ser Asp
                325                 330                 335

Ser Pro Gly Ile Ser Val Gln Val Ser Ser Ile Leu Leu Gly Leu Val
            340                 345                 350

Leu Val Gly Arg Ala Ala Phe Val Phe Pro Leu Ser Phe Leu Ser Asn
        355                 360                 365

Leu Thr Lys Lys Thr Pro Glu Ala Lys Ile Ser Phe Asn Gln Gln Val
```

-continued

```
    370                 375                 380

Thr Ile Trp Trp Ala Gly Leu Met Arg Gly Ala Val Ser Met Ala Leu
385                 390                 395                 400

Ala Tyr Asn Gln Phe Thr Arg Gly Gly His Thr Gln Leu Arg Ala Asn
                405                 410                 415

Ala Ile Met Ile Thr Ser Thr Ile Thr Val Val Leu Phe Ser Thr Val
            420                 425                 430

Val Phe Gly Leu Met Thr Lys Pro Leu Ile Arg Ile Leu Leu Pro Ser
        435                 440                 445

His Lys His Leu Ser Arg Met Ile Ser Ser Glu Pro Thr Thr Pro Lys
    450                 455                 460

Ser Phe Ile Val Pro Leu Leu Asp Ser Thr Gln Asp Ser Glu Ala Asp
465                 470                 475                 480

Leu Glu Arg His Val Pro Arg Pro His Ser Leu Arg Met Leu Leu Ser
                485                 490                 495

Thr Pro Ser His Thr Val His Tyr Tyr Trp Arg Lys Phe Asp Asn Ala
            500                 505                 510

Phe Met Arg Pro Val Phe Gly Gly Arg Gly Phe Val Pro Phe Ala Pro
        515                 520                 525

Gly Ser Pro Thr Asp Pro Val Gly Gly Asn Leu Gln
    530                 535                 540


<210> SEQ ID NO 16
<211> LENGTH: 2553
<212> TYPE: DNA
<213> ORGANISM: Nierembergia hybrida
<220> FEATURE:
<221> NAME/KEY: misc_feature
<222> LOCATION: (1)..(2553)
<223> OTHER INFORMATION: Nucleotide sequence of DNA encoding for protein
      regulating the pH of vacuoles

<400> SEQUENCE: 16

aattattatt atttctctcc aactctcatt tctcagtttg ttgtgacttt ttcagagctt      60

gaagttcagt taattcattt tccaatatat tgattgtttt catttgagcg cgagaggatt     120

tcgtcttctc aatctgcttt caaatccttt ttgtttgtga tattcgatat tattcactca     180

gtttacctta atatttcctc gcactttctg aattcgagtg ctttgaagtg tgttggattt     240

cgaaaagcgg aagaaaattc agcaaaaacg ctgttgctga atttgcagca gtttgagttt     300

ttgctaaata gctaagatct gattgaattt ttcactggtg cttataggga aattcgacgt     360

cgttttgact gcaatatttg tccgtgattc ggactttgtt gaaattttgc tatttgaaat     420

ttgaatgtaa ggttgtcata gctttgccac tcggaaatac agtcagtgag aaagaaaaaa     480

aactgtgtag tgttttttcc acaagtattt ggtgaattga ggttcttgaa atg gcg        536
                                                       Met Ala

ttt gac ttt ggg act ctg ctg gga aag atg aac aac tta aca act tct       584
Phe Asp Phe Gly Thr Leu Leu Gly Lys Met Asn Asn Leu Thr Thr Ser
          5                  10                  15

gat cat caa tca gtg gtg tcg gta aac ttg ttt gtt gca ctt att tgc       632
Asp His Gln Ser Val Val Ser Val Asn Leu Phe Val Ala Leu Ile Cys
     20                  25                  30

gcg tgt att gtg atc ggt cat tta ttg gag gaa aac aga tgg atg aat       680
Ala Cys Ile Val Ile Gly His Leu Leu Glu Glu Asn Arg Trp Met Asn
 35                  40                  45                  50

gag tcc ata act gcc ctt gtg att ggt agt tgc act gga gtc atc att       728
Glu Ser Ile Thr Ala Leu Val Ile Gly Ser Cys Thr Gly Val Ile Ile
                 55                  60                  65
```

-continued

```
cta cta ata agt gga gga aag aac tca cat att tta gtg ttc agc gaa      776
Leu Leu Ile Ser Gly Gly Lys Asn Ser His Ile Leu Val Phe Ser Glu
            70                  75                  80

gat ctt ttc ttc att tac ctt ctt cca ccg atc att ttt aat gct ggg      824
Asp Leu Phe Phe Ile Tyr Leu Leu Pro Pro Ile Ile Phe Asn Ala Gly
        85                  90                  95

ttc cag gtg aaa aag aaa tca ttc ttc cgc aat ttc agt act atc atg      872
Phe Gln Val Lys Lys Lys Ser Phe Phe Arg Asn Phe Ser Thr Ile Met
    100                 105                 110

ctc ttt ggg gca gtt ggc acc ttg ata tcg ttc att att ata tca gcg      920
Leu Phe Gly Ala Val Gly Thr Leu Ile Ser Phe Ile Ile Ile Ser Ala
115                 120                 125                 130

ggt gct att ggc att ttc aag aaa atg gat att gga cac ctt gaa att      968
Gly Ala Ile Gly Ile Phe Lys Lys Met Asp Ile Gly His Leu Glu Ile
            135                 140                 145

gga gat tac ctt gca att gga gca atc ttt gct gca aca gat tct gta     1016
Gly Asp Tyr Leu Ala Ile Gly Ala Ile Phe Ala Ala Thr Asp Ser Val
            150                 155                 160

tgc acc tta caa gtg ctt aat cag gaa gaa aca ccg tta ttg tac agt     1064
Cys Thr Leu Gln Val Leu Asn Gln Glu Glu Thr Pro Leu Leu Tyr Ser
        165                 170                 175

cta gtg ttt gga gaa ggt gtt gtg aat gat gcc aca tct gta gtg ctg     1112
Leu Val Phe Gly Glu Gly Val Val Asn Asp Ala Thr Ser Val Val Leu
    180                 185                 190

ttc aat gct gtc cag aac ttt gac tta tct cat atc agc aca ggc aaa     1160
Phe Asn Ala Val Gln Asn Phe Asp Leu Ser His Ile Ser Thr Gly Lys
195                 200                 205                 210

gct ctg caa tta att gga aac ttt cta tac ttg ttt gcc tcg agc act     1208
Ala Leu Gln Leu Ile Gly Asn Phe Leu Tyr Leu Phe Ala Ser Ser Thr
            215                 220                 225

ttc cta ggg gtt gct gtt ggc cta cta agt gcc ttt ata att aag aaa     1256
Phe Leu Gly Val Ala Val Gly Leu Leu Ser Ala Phe Ile Ile Lys Lys
            230                 235                 240

ctc tac ttt gga agg cac tcg act gat cgt gag gtt gct ata atg ata     1304
Leu Tyr Phe Gly Arg His Ser Thr Asp Arg Glu Val Ala Ile Met Ile
        245                 250                 255

ctc atg gcg tac cta tca tac atg ctt gct gaa tta ttc tat tta agt     1352
Leu Met Ala Tyr Leu Ser Tyr Met Leu Ala Glu Leu Phe Tyr Leu Ser
    260                 265                 270

gga atc ctc act gtg ttt ttc tgt ggg atc gtg atg tct cac tat acc     1400
Gly Ile Leu Thr Val Phe Phe Cys Gly Ile Val Met Ser His Tyr Thr
275                 280                 285                 290

tgg cat aat gtg act gag agc tca aga gtc act acc aag cac acg ttt     1448
Trp His Asn Val Thr Glu Ser Ser Arg Val Thr Thr Lys His Thr Phe
            295                 300                 305

gct aca tta tca ttt att gct gaa ata ttc ata ttc ctt tat gtt ggt     1496
Ala Thr Leu Ser Phe Ile Ala Glu Ile Phe Ile Phe Leu Tyr Val Gly
            310                 315                 320

atg gat gct ttg gac att gag aag tgg aag ttt gta agc gac agc ccc     1544
Met Asp Ala Leu Asp Ile Glu Lys Trp Lys Phe Val Ser Asp Ser Pro
        325                 330                 335

gga aca tca att aag gtc agc tca att ctg cta ggt ctt gtt ttg gtt     1592
Gly Thr Ser Ile Lys Val Ser Ser Ile Leu Leu Gly Leu Val Leu Val
    340                 345                 350

gga agg gga gcc ttt gtt ttc ccc ttg tca ttc ttg tcc aac ttg acc     1640
Gly Arg Gly Ala Phe Val Phe Pro Leu Ser Phe Leu Ser Asn Leu Thr
355                 360                 365                 370

aag aaa aat cct gag gac aag att agc ttt aac cag cag gtt aca ata     1688
Lys Lys Asn Pro Glu Asp Lys Ile Ser Phe Asn Gln Gln Val Thr Ile
```

-continued

```
            375                 380                 385

tgg tgg gct ggg ctt atg cga ggt gct gtt tct atg gcc ctt gct tat      1736
Trp Trp Ala Gly Leu Met Arg Gly Ala Val Ser Met Ala Leu Ala Tyr
            390                 395                 400

aat cag ttt acc agg gga ggt cat act cag tta cgt gcc aat gca ata      1784
Asn Gln Phe Thr Arg Gly Gly His Thr Gln Leu Arg Ala Asn Ala Ile
        405                 410                 415

atg atc acg agt act atc act gtt gtc ctt ttc agc aca gtg gta ttt      1832
Met Ile Thr Ser Thr Ile Thr Val Val Leu Phe Ser Thr Val Val Phe
    420             425                     430

ggg ttg atg aca aaa cct tta att cta tta ttg cta ccc tca caa aaa      1880
Gly Leu Met Thr Lys Pro Leu Ile Leu Leu Leu Leu Pro Ser Gln Lys
435                 440                 445                 450

cac ttg atc aga atg atc tcc tct gaa ccg atg act cca aaa tcc ttc      1928
His Leu Ile Arg Met Ile Ser Ser Glu Pro Met Thr Pro Lys Ser Phe
                455                 460                 465

att gtg cca ctt ctt gac agc aca caa gac tca gaa gct gat ctg ggc      1976
Ile Val Pro Leu Leu Asp Ser Thr Gln Asp Ser Glu Ala Asp Leu Gly
            470                 475                 480

cga cat gta ccc cgt ccc cac agt ttg cgg atg ctc ctg tca acc cca      2024
Arg His Val Pro Arg Pro His Ser Leu Arg Met Leu Leu Ser Thr Pro
        485                 490                 495

tct cac acg gta cat tac tac tgg aga aaa ttt gac aat gca ttc atg      2072
Ser His Thr Val His Tyr Tyr Trp Arg Lys Phe Asp Asn Ala Phe Met
    500                 505                 510

cgt cct gtt ttc ggt gga cga ggt ttt gta cct ttt gtt cca gga tca      2120
Arg Pro Val Phe Gly Gly Arg Gly Phe Val Pro Phe Val Pro Gly Ser
515             520                     525                 530

cct act gaa ccg gtc gaa ccg acc gaa cca aga cca gcc gaa tca aga      2168
Pro Thr Glu Pro Val Glu Pro Thr Glu Pro Arg Pro Ala Glu Ser Arg
                535                 540                 545

cca acc gaa cca act gat gag tgattacact gatggagatg caggttgcac         2219
Pro Thr Glu Pro Thr Asp Glu
            550

taaagtccca ctggccttgg agaaggacga aggcagtttt ttgggtttga ggttttgttt   2279

actgttaata gttttcgaat gtggttaaaa aagggttgtc tagtttttat atataggtcg   2339

cagatacgta atttcagctc agttcccgag gtgaacccct tagaggtttt cttcctgacg   2399

gtttttcttc ttttttgtaa tttatcaaaa acaccaaatg ggtgtatatt ctttaagctt   2459

gtagcttaat taccttataa gcatgtggta gcgttcgtgt aatatgtaaa atttccattg   2519

ccagaaaaga aacttccata caatatttct gccg                                2553


<210> SEQ ID N  O 17
<211> LENGTH: 553
<212> TYPE: PRT
<213> ORGANISM: Nierembergia hybrida
<220> FEATURE:
<221> NAME/KEY: peptide
<222> LOCATION: (1)..(553)
<223> OTHER INFORMATION: Amino acid sequence of protein regulating the
      pH of vacuoles

<400> SEQUENCE: 17

Met Ala Phe Asp Phe Gly Thr Leu Leu Gly Lys Met Asn Asn Leu Thr
                  5                  10                  15

Thr Ser Asp His Gln Ser Val Val Ser Val Asn Leu Phe Val Ala Leu
             20                  25                  30

Ile Cys Ala Cys Ile Val Ile Gly His Leu Leu Glu Glu Asn Arg Trp
         35                  40                  45
```

-continued

```
Met Asn Glu Ser Ile Thr Ala Leu Val Ile Gly Ser Cys Thr Gly Val
     50                  55                  60

Ile Ile Leu Leu Ile Ser Gly Gly Lys Asn Ser His Ile Leu Val Phe
65                  70                  75                  80

Ser Glu Asp Leu Phe Phe Ile Tyr Leu Leu Pro Pro Ile Ile Phe Asn
                85                  90                  95

Ala Gly Phe Gln Val Lys Lys Lys Ser Phe Phe Arg Asn Phe Ser Thr
            100                 105                 110

Ile Met Leu Phe Gly Ala Val Gly Thr Leu Ile Ser Phe Ile Ile Ile
        115                 120                 125

Ser Ala Gly Ala Ile Gly Ile Phe Lys Lys Met Asp Ile Gly His Leu
    130                 135                 140

Glu Ile Gly Asp Tyr Leu Ala Ile Gly Ala Ile Phe Ala Ala Thr Asp
145                 150                 155                 160

Ser Val Cys Thr Leu Gln Val Leu Asn Gln Glu Glu Thr Pro Leu Leu
                165                 170                 175

Tyr Ser Leu Val Phe Gly Glu Gly Val Val Asn Asp Ala Thr Ser Val
            180                 185                 190

Val Leu Phe Asn Ala Val Gln Asn Phe Asp Leu Ser His Ile Ser Thr
        195                 200                 205

Gly Lys Ala Leu Gln Leu Ile Gly Asn Phe Leu Tyr Leu Phe Ala Ser
    210                 215                 220

Ser Thr Phe Leu Gly Val Ala Val Gly Leu Leu Ser Ala Phe Ile Ile
225                 230                 235                 240

Lys Lys Leu Tyr Phe Gly Arg His Ser Thr Asp Arg Glu Val Ala Ile
                245                 250                 255

Met Ile Leu Met Ala Tyr Leu Ser Tyr Met Leu Ala Glu Leu Phe Tyr
            260                 265                 270

Leu Ser Gly Ile Leu Thr Val Phe Phe Cys Gly Ile Val Met Ser His
        275                 280                 285

Tyr Thr Trp His Asn Val Thr Glu Ser Ser Arg Val Thr Thr Lys His
    290                 295                 300

Thr Phe Ala Thr Leu Ser Phe Ile Ala Glu Ile Phe Ile Phe Leu Tyr
305                 310                 315                 320

Val Gly Met Asp Ala Leu Asp Ile Glu Lys Trp Lys Phe Val Ser Asp
                325                 330                 335

Ser Pro Gly Thr Ser Ile Lys Val Ser Ser Ile Leu Leu Gly Leu Val
            340                 345                 350

Leu Val Gly Arg Gly Ala Phe Val Phe Pro Leu Ser Phe Leu Ser Asn
        355                 360                 365

Leu Thr Lys Lys Asn Pro Glu Asp Lys Ile Ser Phe Asn Gln Gln Val
    370                 375                 380

Thr Ile Trp Trp Ala Gly Leu Met Arg Gly Ala Val Ser Met Ala Leu
385                 390                 395                 400

Ala Tyr Asn Gln Phe Thr Arg Gly Gly His Thr Gln Leu Arg Ala Asn
                405                 410                 415

Ala Ile Met Ile Thr Ser Thr Ile Thr Val Val Leu Phe Ser Thr Val
            420                 425                 430

Val Phe Gly Leu Met Thr Lys Pro Leu Ile Leu Leu Leu Leu Pro Ser
        435                 440                 445

Gln Lys His Leu Ile Arg Met Ile Ser Ser Glu Pro Met Thr Pro Lys
    450                 455                 460
```

-continued

Ser Phe Ile Val Pro Leu Leu Asp Ser Thr Gln Asp Ser Glu Ala Asp
465 470 475 480

Leu Gly Arg His Val Pro Arg Pro His Ser Leu Arg Met Leu Leu Ser
485 490 495

Thr Pro Ser His Thr Val His Tyr Tyr Trp Arg Lys Phe Asp Asn Ala
500 505 510

Phe Met Arg Pro Val Phe Gly Gly Arg Gly Phe Val Pro Phe Val Pro
515 520 525

Gly Ser Pro Thr Glu Pro Val Glu Pro Thr Glu Pro Arg Pro Ala Glu
530 535 540

Ser Arg Pro Thr Glu Pro Thr Asp Glu
545 550

<210> SEQ ID NO 18
<211> LENGTH: 2361
<212> TYPE: DNA
<213> ORGANISM: Torenia hybrida
<220> FEATURE:
<221> NAME/KEY: misc_feature
<222> LOCATION: (1)..(2361)
<223> OTHER INFORMATION: Nucleotide sequence of DNA encoding for protein regulating the pH of vacuoles

<400> SEQUENCE: 18
gttggagatt ccgagctgca gcatcacctt gcttatgtaa gctttaaaag tatcagaatt 60
gaatatcgac cactggaaag tgttttagga cttggattct tatctattga gcttgtttga 120
aggtgaaaaa aggctcgatc tcgttcctct atagttggtt ttctggagtt gcaagcgact 180
ctactcggaa tctctttccg ccttattgga agctctgctt tactaaaaaa agtttgtctt 240
tttatctctg attcatcata aaatctgcgg gagattcaga agcggagatc tggtgcccag 300
agcaggagtt tcaactttga gcccgtttat atttataaac aaattccgag tccaaagatt 360
gaactttgaa ataatcaaat aatcaagcaa gcaat atg ggg ttt gaa tct gta 413
Met Gly Phe Glu Ser Val
5 att aag cta gcg gca agt gaa act gac aat ttg tgg agc tct ggt cac 461
Ile Lys Leu Ala Ala Ser Glu Thr Asp Asn Leu Trp Ser Ser Gly His
10 15 20 ggt tca gtg gtc gct ata acc tta ttt gtc act ctt ctc tgc aca tgt 509
Gly Ser Val Val Ala Ile Thr Leu Phe Val Thr Leu Leu Cys Thr Cys
25 30 35 ata gtg att ggt cat ctt ctg gag gaa aac cgt tgg atg aat gaa tct 557
Ile Val Ile Gly His Leu Leu Glu Glu Asn Arg Trp Met Asn Glu Ser
40 45 50 atc att gcc ctc ata att ggt tta gcc acg gga gtt ata atc ctg tta 605
Ile Ile Ala Leu Ile Ile Gly Leu Ala Thr Gly Val Ile Ile Leu Leu
55 60 65 70 ata agt ggt gga aaa agc tcc cat ctc ttg gtg ttc agt gag gat ctt 653
Ile Ser Gly Gly Lys Ser Ser His Leu Leu Val Phe Ser Glu Asp Leu
75 80 85 ttc ttc atc tat gcg ctg cca cca atc att ttt aat gcg ggg ttc caa 701
Phe Phe Ile Tyr Ala Leu Pro Pro Ile Ile Phe Asn Ala Gly Phe Gln
90 95 100 gta aaa aag aaa tca ttc ttt cgc aat ttc gca act ata atg atg ttt 749
Val Lys Lys Lys Ser Phe Phe Arg Asn Phe Ala Thr Ile Met Met Phe
105 110 115 gga gca gtt ggt acc ttg ata tcc ttc atc atc att tca ctc ggt aca 797
Gly Ala Val Gly Thr Leu Ile Ser Phe Ile Ile Ile Ser Leu Gly Thr
120 125 130

-continued

```
att gca ttc ttc ccc aaa atg aac atg aga ctt gga gtt gga gat tat       845
Ile Ala Phe Phe Pro Lys Met Asn Met Arg Leu Gly Val Gly Asp Tyr
135                 140                 145                 150

ctt gct att gga gct att ttt gct gca aca gac tca gtt tgc aca tta       893
Leu Ala Ile Gly Ala Ile Phe Ala Ala Thr Asp Ser Val Cys Thr Leu
                155                 160                 165

cag gtg cta agc cag gac gaa aca cca ctg ttg tac agt cta gtg ttt       941
Gln Val Leu Ser Gln Asp Glu Thr Pro Leu Leu Tyr Ser Leu Val Phe
            170                 175                 180

ggc gag ggt gtt gta aat gac gcg act tca gtg gtc cta ttt aat gca       989
Gly Glu Gly Val Val Asn Asp Ala Thr Ser Val Val Leu Phe Asn Ala
        185                 190                 195

gta cag aac ttc gac ctg cct cat atg tct act gct aaa gct ttc gag      1037
Val Gln Asn Phe Asp Leu Pro His Met Ser Thr Ala Lys Ala Phe Glu
    200                 205                 210

ctt gtt gga aac ttc ttt tat tta ttt gct aca agc act gtg ctg ggt      1085
Leu Val Gly Asn Phe Phe Tyr Leu Phe Ala Thr Ser Thr Val Leu Gly
215                 220                 225                 230

gtt ctg act gga ttg ctt agt gca tac atc ata aaa aag ctc tat ttt      1133
Val Leu Thr Gly Leu Leu Ser Ala Tyr Ile Ile Lys Lys Leu Tyr Phe
                235                 240                 245

gga agg cac tcc act gat cgc gag gtt gcc ata atg ata ctc atg gct      1181
Gly Arg His Ser Thr Asp Arg Glu Val Ala Ile Met Ile Leu Met Ala
            250                 255                 260

tat ctg tcg tat atg tta gct gaa tta ttc gat ttg agc ggt atc ctc      1229
Tyr Leu Ser Tyr Met Leu Ala Glu Leu Phe Asp Leu Ser Gly Ile Leu
        265                 270                 275

acc gtg ttc ttc tgt gga att gtg atg tcg cac tat aca tgg cac aat      1277
Thr Val Phe Phe Cys Gly Ile Val Met Ser His Tyr Thr Trp His Asn
    280                 285                 290

gtc act gaa aac tca aga gtt acc acc aag cat aca ttt gcg aca ttg      1325
Val Thr Glu Asn Ser Arg Val Thr Thr Lys His Thr Phe Ala Thr Leu
295                 300                 305                 310

tca ttt gtt gct gaa ata ttt ata ttt ctg tat gtt ggc atg gat gct      1373
Ser Phe Val Ala Glu Ile Phe Ile Phe Leu Tyr Val Gly Met Asp Ala
                315                 320                 325

tta gac att gag aaa tgg aga ttc gta agc ggc agc atg aca aca tct      1421
Leu Asp Ile Glu Lys Trp Arg Phe Val Ser Gly Ser Met Thr Thr Ser
            330                 335                 340

gca gct gtc agt gca act ctg ctg gga ttg gtt ttg ctc tca aga gca      1469
Ala Ala Val Ser Ala Thr Leu Leu Gly Leu Val Leu Leu Ser Arg Ala
        345                 350                 355

gcc ttt gta ttc cct tta tca ttt ctc tcc aat ctg gcc aaa aag tcc      1517
Ala Phe Val Phe Pro Leu Ser Phe Leu Ser Asn Leu Ala Lys Lys Ser
    360                 365                 370

cca ctc gaa aaa atc agt ctc agg cag caa att ata ata tgg tgg gct      1565
Pro Leu Glu Lys Ile Ser Leu Arg Gln Gln Ile Ile Ile Trp Trp Ala
375                 380                 385                 390

ggt ctt atg cgc gga gcc gtt tcc atg gct ctt gct tac aag cag ttt      1613
Gly Leu Met Arg Gly Ala Val Ser Met Ala Leu Ala Tyr Lys Gln Phe
                395                 400                 405

act aga gaa ggt ctc aca gtg gaa cgt gaa aat gcc ata ttc atc acc      1661
Thr Arg Glu Gly Leu Thr Val Glu Arg Glu Asn Ala Ile Phe Ile Thr
            410                 415                 420

agt aca atc acc att gtg ctc ttc agc act gtg gtg ttt ggt ttg atg      1709
Ser Thr Ile Thr Ile Val Leu Phe Ser Thr Val Val Phe Gly Leu Met
        425                 430                 435

acg aag ccc ctc atc aat tta ctg ata ccc tca cca aag ctt aac aga      1757
Thr Lys Pro Leu Ile Asn Leu Leu Ile Pro Ser Pro Lys Leu Asn Arg
    440                 445                 450
```

-continued

```
tcg gtc tct tca gaa ccg ctg act cca aac tcc atc aca atc cca ctt     1805
Ser Val Ser Ser Glu Pro Leu Thr Pro Asn Ser Ile Thr Ile Pro Leu
455                 460                 465                 470

ctc ggg gaa agt cag gac tct gtg gcc gaa cta ttc agc atc aga ggt     1853
Leu Gly Glu Ser Gln Asp Ser Val Ala Glu Leu Phe Ser Ile Arg Gly
                475                 480                 485

caa act tca caa ggt ggc gaa ccc gtt gct cga ccg agc agc cta cgc     1901
Gln Thr Ser Gln Gly Gly Glu Pro Val Ala Arg Pro Ser Ser Leu Arg
            490                 495                 500

atg tta ctc aca aag ccc act cat acg gtg cac tat tat tgg aga aaa     1949
Met Leu Leu Thr Lys Pro Thr His Thr Val His Tyr Tyr Trp Arg Lys
        505                 510                 515

ttc gac aat gct ttt atg cgt ccg gtc ttt ggt ggg cgt ggc ttt gta     1997
Phe Asp Asn Ala Phe Met Arg Pro Val Phe Gly Gly Arg Gly Phe Val
    520                 525                 530

cca tat gtt ccc ggt tca ccg act gaa cga agc gtt cgc aac tgg gaa     2045
Pro Tyr Val Pro Gly Ser Pro Thr Glu Arg Ser Val Arg Asn Trp Glu
535                 540                 545                 550

gaa gag acc aaa cag taaaaagatt ttcttgtgtg aatgatggtg aagagattag     2100
Glu Glu Thr Lys Gln
                555

attctttgga tattcgtttt tcttatttct aatgtgtcac ctgggaagtt gttgaatgaa   2160

attatattat cgtctggttt tcgactttgc gcttgtggaa ggaatatttc ttctggattt   2220

tgcatggaaa cctcaatgat aggggggtgtg atatttttgt tagaaactga gtcgtttgat   2280

gtatattgtt ggtaatgcag ctgggttttg ttttgtatgt atagtcatca agtgtgtatt   2340

tattcatatt gttatgcagt c                                             2361


<210> SEQ ID NO 19
<211> LENGTH: 555
<212> TYPE: PRT
<213> ORGANISM: Torenia hybrida
<220> FEATURE:
<221> NAME/KEY: peptide
<222> LOCATION: (1)..(555)
<223> OTHER INFORMATION: Amino acid sequence of protein regulating the
      pH of vacuoles

<400> SEQUENCE: 19

Met Gly Phe Glu Ser Val Ile Lys Leu Ala Ala Ser Glu Thr Asp Asn
                5                   10                  15

Leu Trp Ser Ser Gly His Gly Ser Val Val Ala Ile Thr Leu Phe Val
            20                  25                  30

Thr Leu Leu Cys Thr Cys Ile Val Ile Gly His Leu Leu Glu Glu Asn
        35                  40                  45

Arg Trp Met Asn Glu Ser Ile Ile Ala Leu Ile Ile Gly Leu Ala Thr
    50                  55                  60

Gly Val Ile Ile Leu Leu Ile Ser Gly Gly Lys Ser Ser His Leu Leu
65                  70                  75                  80

Val Phe Ser Glu Asp Leu Phe Phe Ile Tyr Ala Leu Pro Pro Ile Ile
                85                  90                  95

Phe Asn Ala Gly Phe Gln Val Lys Lys Lys Ser Phe Phe Arg Asn Phe
            100                 105                 110

Ala Thr Ile Met Met Phe Gly Ala Val Gly Thr Leu Ile Ser Phe Ile
        115                 120                 125

Ile Ile Ser Leu Gly Thr Ile Ala Phe Phe Pro Lys Met Asn Met Arg
    130                 135                 140
```

-continued

```
Leu Gly Val Gly Asp Tyr Leu Ala Ile Gly Ala Ile Phe Ala Ala Thr
145                 150                 155                 160

Asp Ser Val Cys Thr Leu Gln Val Leu Ser Gln Asp Glu Thr Pro Leu
                165                 170                 175

Leu Tyr Ser Leu Val Phe Gly Glu Gly Val Val Asn Asp Ala Thr Ser
            180                 185                 190

Val Val Leu Phe Asn Ala Val Gln Asn Phe Asp Leu Pro His Met Ser
        195                 200                 205

Thr Ala Lys Ala Phe Glu Leu Val Gly Asn Phe Phe Tyr Leu Phe Ala
    210                 215                 220

Thr Ser Thr Val Leu Gly Val Leu Thr Gly Leu Leu Ser Ala Tyr Ile
225                 230                 235                 240

Ile Lys Lys Leu Tyr Phe Gly Arg His Ser Thr Asp Arg Glu Val Ala
                245                 250                 255

Ile Met Ile Leu Met Ala Tyr Leu Ser Tyr Met Leu Ala Glu Leu Phe
            260                 265                 270

Asp Leu Ser Gly Ile Leu Thr Val Phe Phe Cys Gly Ile Val Met Ser
        275                 280                 285

His Tyr Thr Trp His Asn Val Thr Glu Asn Ser Arg Val Thr Thr Lys
    290                 295                 300

His Thr Phe Ala Thr Leu Ser Phe Val Ala Glu Ile Phe Ile Phe Leu
305                 310                 315                 320

Tyr Val Gly Met Asp Ala Leu Asp Ile Glu Lys Trp Arg Phe Val Ser
                325                 330                 335

Gly Ser Met Thr Thr Ser Ala Ala Val Ser Ala Thr Leu Leu Gly Leu
            340                 345                 350

Val Leu Leu Ser Arg Ala Ala Phe Val Phe Pro Leu Ser Phe Leu Ser
        355                 360                 365

Asn Leu Ala Lys Lys Ser Pro Leu Glu Lys Ile Ser Leu Arg Gln Gln
    370                 375                 380

Ile Ile Ile Trp Trp Ala Gly Leu Met Arg Gly Ala Val Ser Met Ala
385                 390                 395                 400

Leu Ala Tyr Lys Gln Phe Thr Arg Glu Gly Leu Thr Val Glu Arg Glu
                405                 410                 415

Asn Ala Ile Phe Ile Thr Ser Thr Ile Thr Ile Val Leu Phe Ser Thr
            420                 425                 430

Val Val Phe Gly Leu Met Thr Lys Pro Leu Ile Asn Leu Leu Ile Pro
        435                 440                 445

Ser Pro Lys Leu Asn Arg Ser Val Ser Ser Glu Pro Leu Thr Pro Asn
    450                 455                 460

Ser Ile Thr Ile Pro Leu Leu Gly Glu Ser Gln Asp Ser Val Ala Glu
465                 470                 475                 480

Leu Phe Ser Ile Arg Gly Gln Thr Ser Gln Gly Gly Glu Pro Val Ala
                485                 490                 495

Arg Pro Ser Ser Leu Arg Met Leu Leu Thr Lys Pro Thr His Thr Val
            500                 505                 510

His Tyr Tyr Trp Arg Lys Phe Asp Asn Ala Phe Met Arg Pro Val Phe
        515                 520                 525

Gly Gly Arg Gly Phe Val Pro Tyr Val Pro Gly Ser Pro Thr Glu Arg
    530                 535                 540

Ser Val Arg Asn Trp Glu Glu Glu Thr Lys Gln
545                 550                 555
```

-continued

<210> SEQ ID NO 20
<211> LENGTH: 6298
<212> TYPE: DNA
<213> ORGANISM: Ipomea nil
<220> FEATURE:
<221> NAME/KEY: misc_feature
<222> LOCATION: (1)..(6298)
<223> OTHER INFORMATION: Nucleotide sequence of promoter region of gene encoding for protein regulating the pH of vacuoles

<400> SEQUENCE: 20
gatctcagtc tgtggatgtc ctagagacat tcatatttga agttgagagt tagctaaata 60
gaaaggtaaa gacaattgga tcatataaag gtgatgagta ttatgggaaa ccatcaaaag 120
ttgggcaaat tcccgtccca tttaagaaat tcctcgaatc taaaggcatt tgtgcataat 180
acacaatgtc aggcacacca caacaaaatg gtgtggaaga aaggtgaaat cgtactctaa 240
gggaaatggt taggagttag gtaaataatt gtacattgct tgtttcattg tggatatatg 300
cattaaaaac aacagcatac ttactcaata gggttcctag taaggttgtt ttttaaaaca 360
ccttatgaac tgtggacaag aaggaaacct agtttgagac atcttcacat tcagggttgt 420
caagctggag tgatgatata taatccacat gaaaataaat tatggatatc cagaaccatt 480
aatggttatt tcattggata tccagaaagg tctaaaggta catgtttatt gtcctaatca 540
taagtacgag gattgttgag tctggtaatg ctcgcttcat ttaaaatggc gaagtcagtg 600
ggagtgtggg agctcgtaat gttaaaatta aggagtcatt gatggttcta gattcatcaa 660
gtgatccttt tttcctgttg ttgttcctat tgttgcagtg cagtgtagcc ttatggaaat 720
actttggaac aacagcaact agatgctcaa attccacatg aggaagctat tgtaaatgaa 780
gatgaggttg aaactcaaga tgatgatcaa gtgaaatctc agcaggaagt gacattaagg 840
aggtctacta tagatagaaa agatcaacca ttcttgatga ctatattgtt tatacacttg 900
agcattgata attatccagt ctcatttaac caagccatac aggataataa ttctccttga 960
ggattatttt ggttttggtg gctcattctg ttcttgagct ccaccaaatg gttgttaaaa 1020
ttacctttct gaatggtaaa ttaaaagagg aagtatacat ggattagccg taaggcttca 1080
tggccacagg aaaggaaaat ctggtatgta gattgaagat gtcgatctat ggattaaaac 1140
atgcttctag acaatggtac ttgagattgt catttggttt tgtagagatc actgttgatc 1200
ggtgtatcca cataaaggtt taatggaagc aagtttgtaa tcctagtatt acatgttaac 1260
gacattcttc ttgctgctaa taataaaagg gatgttgcgt gatgttaagg aatagctttc 1320
taagaacttt gaaatgaagg atatgggtga gacttcatat gtgattggaa taagaaatat 1380
tccgtaatag atcacatggg attttaggtt catcctagaa gactcacatt aacaaagttt 1440
tagaaagata caaactggaa atctgcaaag agggtcctgt gatacttaca aggcactaag 1500
gaccacatgc tcacctataa aatgaacgaa taacctagag gttataggtt attcggattc 1560
agactatgcc ggatgtttgg atacccgaaa atccacattc gaatatattt ttccacttgc 1620
tcgtggagca atatcttgga tgagtgtgaa ggagcctgtc attgctactt ccactataag 1680
ggcagaattt gtagcatgct ttgaggctag tagacactat aaaaattggc tgccttgtgc 1740
caacatcatt tgcatccagc tataagcatc tccattttcg aacatcattc gattcttata 1800
gctggatgaa gatgattcac tgcactttgg ttgcatattg aagctgcgat tgctatcgaa 1860
aacaaataac ctatctatat aaaacaaacg acttagattt agggaataag aaggaagata 1920 cttttttaa aatcccaaaa ttacctttta ggtttgacct gcaaataaca ctttaagatc 1980
aaatcagata aaatgtcata atcaatgatc aaattgaata attttagtag tcgaggatca 2040

-continued

```
aattggtaaa atccccatag tcgagggact aaaccagtaa ttttctcgcg tttgaacgtt   2100
tgtccgaaaa ttggcattag cgatagctta attgagtttt tcaattctct aattttttaa   2160
attttgtttc ttcataaaat ccttcacttt ttcactttgc taatattttg ccgaatttat   2220
aatatttcca atttctaaag tagcagaacc ccagacgttg aactgccaat tttttttttt   2280
gtttttgttt tttgtttttt tatttcctta tccctccacc tcattttgaa gttaattatt   2340
attattaatt cattaatttt taaaatagag agactgcatt aacacaaaat tagccaatta   2400
ggtagcagaa ttaaatttaa acaaacaagt tggtttaatg taatttttgt caatttaatt   2460
tctctatttt tggacaaaaa ttaggtagac ttattaaatt aaataaacat gtttgtttaa   2520
ttttacttct tctacctaag tttgtgtcaa ttcagtctct ctattttata aattaatgaa   2580
tggttaaata taacttataa gtgcattgtg tccaaatgat cacaagagtt aggccaactt   2640
ctttttttcat ataggtgatt ctttttttcga gtattacgta cacttcagtc ttgtcaacta   2700
acacttagaa tttagttgtc attttcgaac ataggtgtca actaagtttg gtatccacta   2760
tatagcacat gtattccaag agatttaatc tcattcatca tgacaacttc tctaccaatt   2820
ctttgctcaa tcttttagtt agcgaattcg ctatattatc ctataacttt cagtatagtc   2880
aacaaaaata aaatgtattg caagaaacta tttaatagtg tatgttatgt atatgtccta   2940
tatgtctaga cttaccgtta tacatattac taatttacta tatgtccttc caattgcgaa   3000
ttgactatcg taatgcatac atattggaga tatatatttt ttctaggggt aaatgcaggt   3060
tggatcgacc cattaggcct gccccaacgc aaactttttt tgtcgggctt ttgcggaccg   3120
gcttgcgggt tagaaaatac acagcccaag cccgtccatg cgggctcgcg ggccttattt   3180
caaaaaaaaa aaaaatacta cgtattattc tattatttta tattcaaata gtctaatata   3240
aataaataaa aaaatcgtgt ttgaaaatta cttttttttt tatatatatt ttttaaaatt   3300
ttaatgttat atacgaagtg tgtgtaatat atatatatat atatatatat atatatatat   3360
atatatatat atatatatat attatttata ttatttatat ttatgtttat atttaaatac   3420
gggcatggct cgtcggctgg tccgttaggt ccgctctttt gtaggccatt tttttgtgtg   3480
accctaaatc gtctcaccgc gggacaagta tagggcagct tgcggacttc ggtccatttt   3540
gacatatata tatatatata tatatatata tatatatata tatatatata tatatatata   3600
tatatatata taacattaaa atttaaaaaa tatagatttt ttttaaacat gaaaaaaatt   3660
aatattattt atattaaatt atttgaatat aaaataaata atactttttt atagcttgcg   3720
ggctggtcca taaaagcccg taaaaagaat acgttggggt tggcctaatg gaccgatcca   3780
acccgcattg acacccatag gaaaaacatc tatctccaat ttgtatgcat tacaatagtc   3840
aatttgcaat tggaagagca tatagtaatt agtaatatgt ataacggtaa gtctagacat   3900
attgaacatg tacataatac tattaaatag cttcttgcaa taggttttat ttttgttgac   3960
tatacatgaa gttataggat aatatagcga attcacaaac taaaagattg agcaatgagt   4020
tagtagaaaa gttgtcatga tggatgagat taaatctctt ggaatacatg tgctagtgga   4080
taccaaactt agctgacacc tatgttcgaa aatgacaact aaattctact acgtaagtgt   4140
tagttgacaa agtagagtgt actgaatact cgaaaaaaga atcagttatg tgaaaaaaaa   4200
aagttggcct aactcttgtg atcattttag acacaatgca cttataagtt atactagtat   4260
tttttatgcg cgatgcacaa aaaatagttg cacaatatta atacattata ttaaaatttt   4320
aaatttattt agattttaga tatttaaatt gttctaacta ataatactaa taataataat   4380
```

-continued

```
gtaaataatt tttataaatt tcagatttat atttaggtaa taattaacat ataactcaaa   4440
tatataatgt gtatatatta ttattaaggg aaaatgacac tttttttccc tgagttatat   4500
accacttttt ttcccttgag ttatttaagt ggctcttttc cccctaaaat gttaaatgga   4560
catattaacc cttaaaataa atatttcaaa taaatatttc atttattttt cttctctaac   4620
aaattattac tataatttgg ttcaaaccaa acagatacta tagcaaccaa accaaaatat   4680
tccaattaca atttagaatc aaaacgcgat atttaaagtt tattaaaatt gcaaatcgga   4740
atggtcggtt catgttccga actgaaaaaa taaaatacat ttattgttga atttagacta   4800
ttttaaaata aaaaataaaa caaaatttta aaataaagac ggttcaaaat cgcgaaccga   4860
atccggaacc gccggttcac ggttcatgat ccagtttttt tggttcataa aatttaataa   4920
attgaaatct aaatattgga ttctagatct gaatcataac cgaaaacttt taattcgatt   4980
actatagtgt ccggttcagt tcgaaccgaa ccgtggtcat tgctacatat acacaataat   5040
ttgttggaga aattaaataa ataaaatgtt tactttaagg gtagaaatgt caatttaata   5100
tttcgggggg aaaaccacca cttttaaatt aattgagggg gctaatgtgc ttatataaat   5160
ataattgagg ggaaaaagtg gtataagtat ataacttagg gggaaaaaat gtcattttcc   5220
ctattattaa tgaagaagat aagaaaatat atggtgaatg catgtgcctt tatagcataa   5280
tgtacaaaaa aaacttaacg aaaaaaacaa acataaataa ggggtataac tttcattcac   5340
acttattatg tttttagatt agatttaacc atacatgcat taatttgtaa aatagcgaga   5400
gtgaattaac acaaaattag gtagaagaag taaaattaaa caaacatgtt tatttaattt   5460
aacaagtcca cctaattttt gtccaaaaat agagaaatta aattgacaaa aattacatta   5520
aacaaacttg tttgtttaaa ttgaattctt ctacctaatt ggctaatttt gtgttaatgc   5580
agtctctcta ttttaaaaat taatgaatta ataataataa ttaacttcaa aatgaggtgg   5640
agggataagg aaataaaaaa acaaaaaaca aaaacaaaaa aaaaaaattg gcagttcaac   5700
gtctggggtt ctgctacttt aaatactgat aggagagttg tcgttcattt tacaagtatt   5760
aaggatgtac acgtattgag aatgtaggct acagaaattt tcagacagat agatacataa   5820
atccgtataa tagagacaga gaaacagaaa aagagagagt cacgttaatc ctgagatttt   5880
cctccatttg tctgaagctc ttcatccttc aacactaccc ccacatctca cctttcaagg   5940
tccaatcttt atcattcatc tttaatttcc agctctatct tgggatttgc atgtaaattt   6000
tatttatttt tcgggtttct gtttccgatc ttatgctttt gttccaaagg gtatttgatt   6060
tcatatatta tgagttttgc atgcattttc tcttttgtaa aatgaaagaa aatttgagat   6120
attggtgggt ttgatctgaa agtttgtttg tttgcagtga tttgtatgtt ttcgggaggg   6180
attggaatgg gcaacccgga tatgtgaaca gaaaccacga cattgggaaa agatttattg   6240
caaaaattgt tttgattgtt ttggattttg tggtagaaaa aggggaagaa caaaaatg     6298
```